US006916305B2

(12) United States Patent
Jones et al.

(10) Patent No.: US 6,916,305 B2
(45) Date of Patent: *Jul. 12, 2005

(54) METHOD OF LOADING DRUG DELIVERY PACK

(75) Inventors: Eugene C. Jones, San Diego, CA (US); Michael A. Taylor, Napa, CA (US)

(73) Assignee: Prismedical Corporation, Napa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/339,715

(22) Filed: Jan. 8, 2003

(65) Prior Publication Data

US 2003/0100860 A1 May 29, 2003

Related U.S. Application Data

(62) Division of application No. 09/559,692, filed on Apr. 27, 2000, now Pat. No. 6,527,738.
(60) Provisional application No. 60/132,088, filed on Apr. 30, 1999.

(51) Int. Cl.⁷ .............................................. A61M 37/00
(52) U.S. Cl. .............................. 604/84; 604/85; 604/89
(58) Field of Search ............................ 604/82, 84, 85, 604/89, 80, 251, 252; 34/284, 288, 296, 297

(56) References Cited

U.S. PATENT DOCUMENTS

| | | |
|---|---|---|
| 3,276,458 A | 10/1966 | Iversen et al. |
| 3,517,816 A | 6/1970 | Huppen |
| 3,730,349 A | 5/1973 | Herrmann |
| 4,070,289 A | 1/1978 | Akcasu |
| 4,160,727 A | 7/1979 | Harris, Jr. |
| 4,231,872 A | 11/1980 | Keil |
| 4,280,912 A | 7/1981 | Berry, III et al. |
| 4,396,383 A | 8/1983 | Hart |
| 4,458,733 A | 7/1984 | Lyons |
| 4,484,920 A | 11/1984 | Kaufman |
| 4,507,114 A | 3/1985 | Bohman et al. |
| 4,540,410 A | * 9/1985 | Wood et al. .................. 604/82 |
| 4,576,603 A | 3/1986 | Moss |
| 4,648,978 A | 3/1987 | Makinen et al. |
| 4,698,153 A | 10/1987 | Matsuzaki et al. |
| 4,784,763 A | 11/1988 | Hambleton et al. |

(Continued)

*Primary Examiner*—Edward K. Look
*Assistant Examiner*—Michael Leslie
(74) *Attorney, Agent, or Firm*—Knobbe Martens Olson & Bear LLP

(57) ABSTRACT

Several improvements are disclosed for a drug delivery pack with dry reagent in a housing, each of which can be employed independently or in conjunction with others of the improvements. A novel spring is provided with two spring columns extending in parallel between a spring top and a spring bottom. The spring is particularly designed for fitting within the housing and compacting a dry reagent bed. A plunger mechanism to ratchet housing portions between two positions. In one position, a compression component adjacent the reagent bed is relatively uncompressed, such that it does not "set" over time. When the user is about to use the drug delivery device, the plunger is slid to compress the compression component so that it exerts pressure on the reagent bed. A similar sliding mechanism can also divert a stream of diluent through the housing from a priming path, where diluent bypasses the reagent bed, to a functional path passing through and eroding the reagent bed. Additionally, a method is provided for lyophilizing a liquid form of reagent within the housing from which it is to be delivered, thereby avoiding separate lyophilization and separate loading of dry form of the reagent.

9 Claims, 20 Drawing Sheets

U.S. PATENT DOCUMENTS

| | | |
|---|---|---|
| 4,810,388 A | 3/1989 | Trasen |
| 4,871,463 A | 10/1989 | Taylor et al. |
| 4,994,056 A | 2/1991 | Ikeda |
| 5,004,535 A | 4/1991 | Bosko et al. |
| 5,032,265 A | 7/1991 | Jha et al. |
| 5,059,317 A | 10/1991 | Marius et al. |
| 5,163,922 A | 11/1992 | McElveen, Jr. et al. |
| 5,259,954 A | 11/1993 | Taylor |
| 5,429,603 A | 7/1995 | Morris |
| 5,435,076 A * | 7/1995 | Hjertman et al. ............. 34/296 |
| 5,637,087 A | 6/1997 | O'Neil et al. |
| 5,685,846 A | 11/1997 | Michaels, Jr. |
| 5,725,777 A | 3/1998 | Taylor |
| 5,752,940 A * | 5/1998 | Grimard ...................... 604/82 |
| 5,807,323 A | 9/1998 | Kriesel et al. |
| 6,527,738 B1 * | 3/2003 | Jones et al. ................... 604/84 |

\* cited by examiner

METHOD OF LOADING DRUG DELIVERY PACK

REFERENCE TO RELATED APPLICATION

This application is a divisional of U.S. application Ser. No. 09/559,692, filed Apr. 27, 2000 now U.S. Pat. No. 6,527,738, and claims the priority benefit under 35 U.S.C. § 119(e) from provisional Application No. 60/132,088 of Jones et al., filed Apr. 30, 1999.

BACKGROUND OF THE INVENTION

1. Field of the Invention

The present invention relates generally to drug delivery devices, and more particularly to devices for storing, transporting and dissolving dry reagents.

2. Description of the Related Art

Medical treatments often involve solutions or suspensions of drugs or other reagents. Transporting and storing such solutions can be extremely expensive. Accordingly, it is advantageous to transport and store drugs or other reagents in a dry powdered or lyophilized form, reducing the bulk and weight, and to mix the reagents with a fluid just prior to administration.

U.S. Pat. No. 5,259,954 to Taylor, issued Nov. 9, 1993 (hereinafter "the '954 patent") and U.S. Pat. No. 5,725,777, issued Mar. 10, 1998 (hereinafter "the '777 patent") disclose a drug pack or "reagent module" suitable for storing dry reagents and for preparing solutions for administration by passing a fluid through the pack. Specifically, FIGS. 9–10 and 12–15 of the '777 patent illustrate two embodiments in which a porous compression element constantly exerts an inward force on the dry reagent bed, keeping the reagents compacted even as the bed is eroded by passing fluid through the porous compression element and through the bed. This arrangement advantageously enables efficient, uniform dissolution of the reagent bed.

While the reagent modules of the '954 and '777 patents operate well in storing and dissolving reagent beds efficiently, there remains room for improvement. Specifically, automated assembly of the disclosed compression elements is difficult, tending to result in mis-orientation and tangling. Furthermore, the foam compression elements disclosed in the '954 patent are difficult to disinfect and tend to retain any contaminants they are exposed to prior to assembly and during operation.

Accordingly, a need exists for improved drug delivery packs of the type disclosed in the '954 and '777 patents.

SUMMARY OF THE INVENTION

In satisfaction of this need, the present application provides a number of improvements over prior drug delivery packs. As the skilled artisan will readily appreciate from the disclosure herein, the improvements described herein can be employed in conjunction or independently of one another.

In accordance with one aspect of the present invention, an apparatus for delivering reagent in fluid form is provided. The apparatus includes a housing defining a fluid inlet and a fluid outlet, the housing including a slide mechanism movable between a first position and a second position. At least one dry reagent bed is housed within the housing. A compression component is positioned within the housing to compact the reagent bed in at least the second position. The slide mechanism engages and compresses the compression component in the second position, as compared to the first position.

In accordance with another aspect of the present invention, a method is provided for preparing a reagent delivery device for delivery of fluid form of reagent from dry form of the reagent. The method includes providing a reagent bed and a compression component enclosed within a housing. Subsequently the compression component is compacted to exert pressure on the reagent bed.

In accordance with another aspect of the present invention, a device is provided for delivering fluid form of a dry reagent housed therein. The device includes a housing that defines a fluid inlet and a fluid outlet. A dry reagent bed is housed within the housing and a compression component is positioned within the housing to exert pressure upon the dry reagent bed. The compression component includes a top end, a bottom end, and at least two spring elements that extend parallel along a spring axis between the top end and the bottom end.

In accordance with another aspect of the present invention, a spring is provided for reciprocation within a bore. The spring includes a top platform and a bottom platform, each with perforations for fluid flow therethrough. The spring additionally includes at least one spring column that extends between the top platform and the bottom platform. The spring column comprising a series of alternating loops along a spring axis.

In accordance with another aspect of the present invention, a reagent delivery device is provided. The device includes a dry reagent bed and a housing enclosing the dry reagent bed. The housing has a fluid inlet and a fluid outlet. A ratcheting mechanism allows at least two housing components to slide with respect to one another between a first locking position and a second locking position. In the first locking position, the housing defines a first fluid flow path between the inlet and the outlet, which path excludes the reagent bed. In the second locking position, the housing defines a second fluid flow path between the inlet and the outlet, which path includes the reagent bed.

In accordance with another aspect of the present invention, a method is provided for delivering a fluid form of a reagent from a dry form of the reagent within a housing. The method includes initially flowing a fluid through the housing but outside the reagent bed. A flow path is then altered to direct the fluid through the reagent bed.

In accordance with another aspect of the present invention, a method is provided for forming a device for delivering a fluid form of a reagent from a dried form of the reagent. The method includes lyophilizing an initial fluid form of the reagent within the device.

BRIEF DESCRIPTION OF THE DRAWINGS

These and other aspects of the invention will be apparent to the skilled artisan from the detailed description of the preferred embodiments below and the appended drawings, which are meant to illustrate and not to limit the invention, and wherein.

DETAILED DESCRIPTION OF THE PREFERRED EMBODIMENT

Figure 1A:
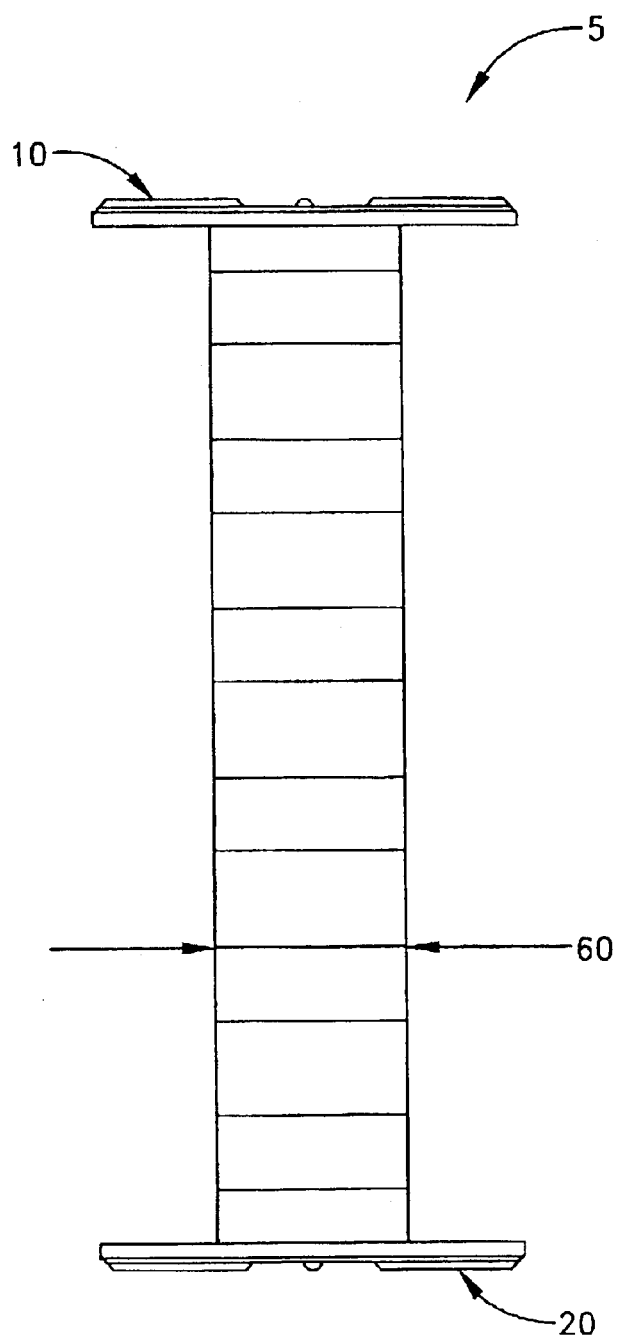
FIG. 1A is a side elevational view of a spring, constructed in accordance with a first embodiment of the invention.

As noted in the Background section above, U.S. Pat. No. 5,259,954, issued Nov. 9, 1993 (hereinafter "the '954 patent") and U.S. Pat. No. 5,725,777, issued Mar. 10, 1998 (hereinafter "the '777 patent"), each issued to Taylor, disclose drug packs for reagent modules suitable for storing dry reagents. Flowing a diluent fluid through the packs forms medical solutions. The disclosures of the '954 and the '777 patent are incorporated herein by reference. While the features and aspects of the invention described herein are particularly suitable for utilization in drug packs of the type disclosed in the '954 and '777 patents, the skilled artisan will readily find applications for many of the principles disclosed herein in other contexts.

Elastomeric Spring

FIGS. 1A to 1D illustrate an elastomeric spring 5, constructed in accordance with a preferred embodiment of the invention. While described in the context of a particular drug delivery pack, the skilled artisan will find application for the disclosed spring design in a number of other contexts. The spring is particularly advantageous for applications where it is desirable to have bio-compatibility, a constant spring rate through a range of compression states and even pressure across the width of the spring.

As shown in FIGS. 1A to 1D, the spring 5 includes a top end 10, a bottom end 20, and at least one, preferably a plurality of adjacent and generally parallel spring columns 30, 40 (two in the illustrated embodiment) extending between the ends 10, 20. Each of the spring columns 30, 40 comprises a series of undulating folds or loops 35, 45 along the spring axis. Each column 30, 40 has the shape that would be obtained if a planar strip of material were folded in alternating directions, in zigzag or accordion fashion, down the length of the strip. The loops 30, 40 can thus be considered the peaks and troughs of a waveform. In one embodiment, the spring columns 30, 40 can be joined at a bridge 50 between adjacent inner loops 35, 45, to maintain even pressure on both sides of the spring 5.

The spring 5 has a fairly uniform spring rate at various degrees of compression, due to the illustrated cylindrical configuration of the loops 35, 45 and even distribution of these loops along the length of the columns 30, 40. By modifying the loop configurations, various other spring rates can be achieved. For example, the loops (or peaks/troughs of a waveform) can have a variety of-geometries. The waveforms preferably have curved peaks and troughs. Most preferably, the loops 35, 45 have the illustrated cylindrical configuration for consistent spring rate at various compression levels, though other configurations (e.g., elliptical, parabolic, hyperbolic or any other smooth curvatures) will demonstrate good results as well. In still other arrangements, the spring columns 30, 40 can have a sawtooth waveform (alternating folds having sharp peaks and troughs), which can advantageously compress further, enabling a smaller overall size of the drug delivery pack. Such an arrangement, on the other hand, would not distribute stress as evenly as the illustrated loops, and would rather tend to focus stress at sharp corners of the folds. The spring rates can also be increased significantly by connecting the inner loops of the right and left columns (as shown at bridge 50), by utilizing denser material or by utilizing thicker columns.

Figure 1B:
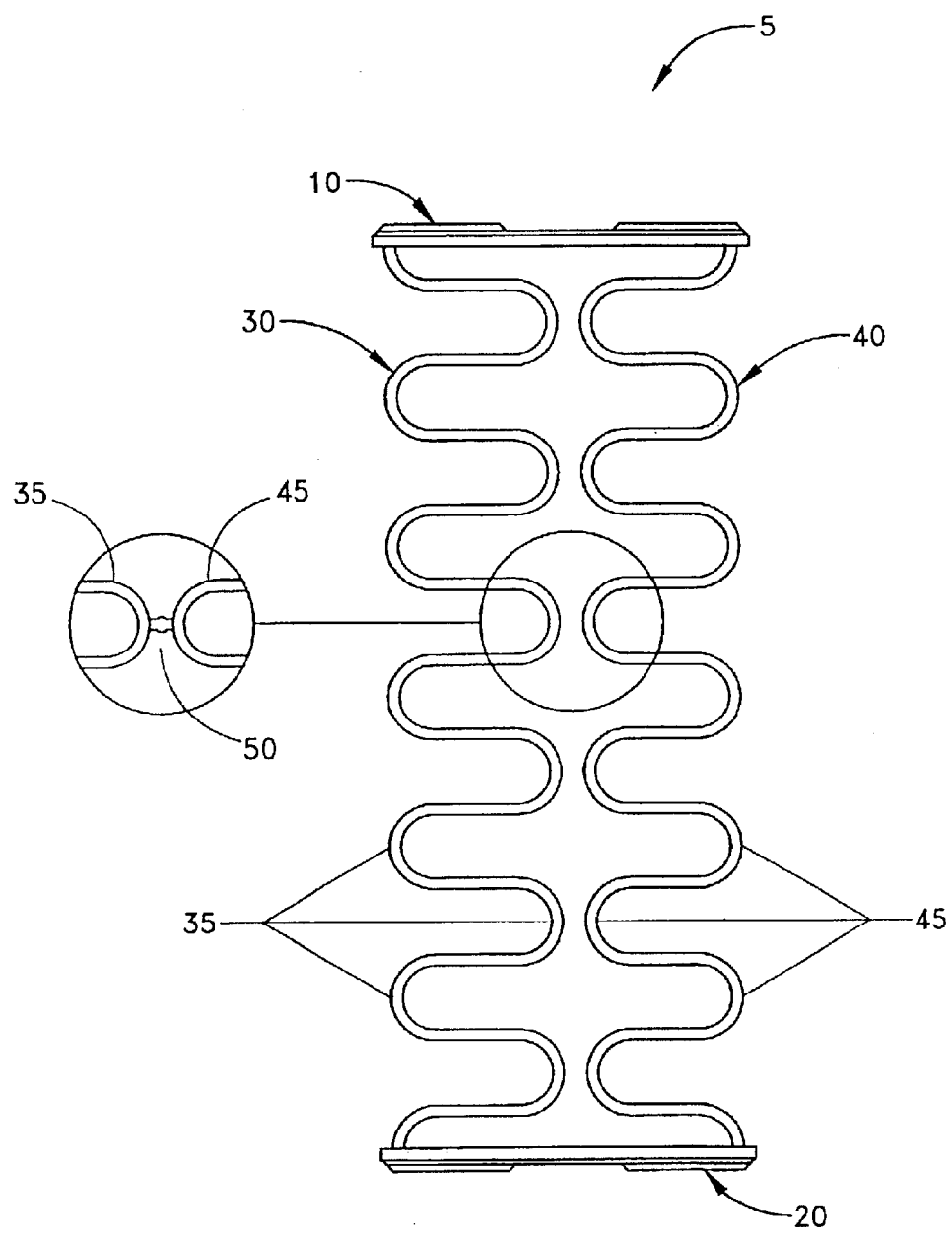
FIG. 1B is a front elevational view of the spring in FIG. 1A.
Figure 1C:
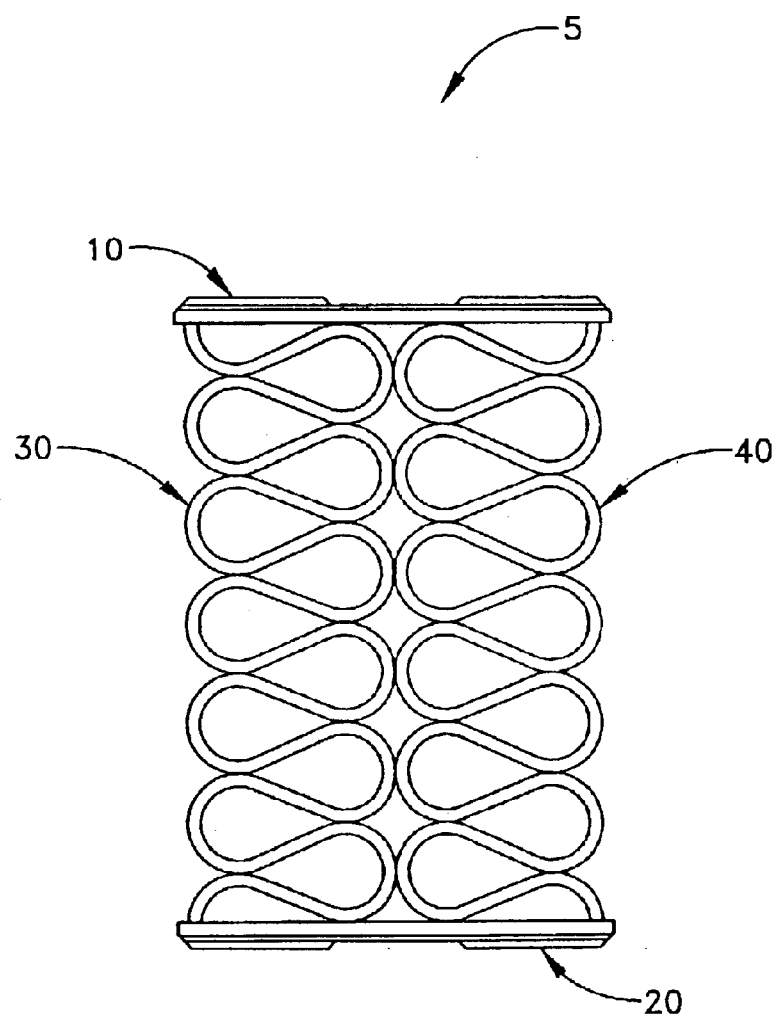
FIG. 1C is a front elevational view of the spring of FIG. 1B in a fully compressed position.

With reference to FIGS. 1B and 1C, during compression, the spring 5 expands radially until the inner loops 45 of the right spring 40 and the loops 35 of the left spring 30 contact one another. The outer loops 35, 45 expand to have about the same width of, or slightly larger than, the ends 10, 20. Vertically adjacent loops contact one another in the fully compressed (solid height) condition, leaving the volume of the loops themselves to absorb any excess external pressure. A depth 60 (FIG. 1A) of the columns 30, 40, in a dimension orthogonal to each of the width and height, is significantly less than the maximum width of the ends 10, 20.

Figure 1D:
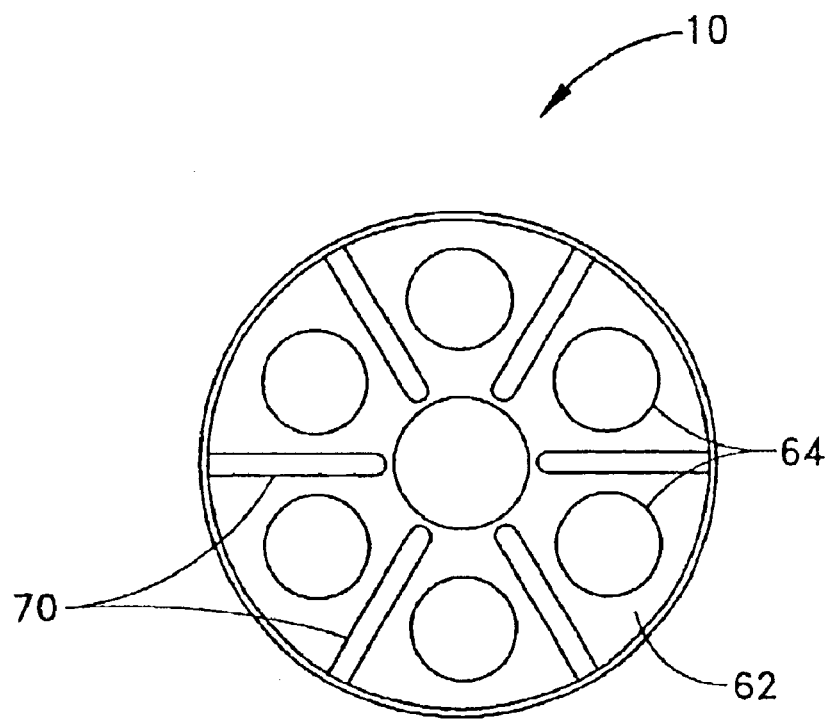
FIG. 1D is a top plan view of the spring of FIG. 1A.

Referring to FIGS. 1B and 1D, each end 10, 20 includes a platform 62 preferably having a plurality of perforations 64 therein for the illustrated embodiment. Additionally, the platform includes a plurality of protrusions in the form of ribs 70 that are advantageous for the illustrated drug delivery pack discussed below. Each of the top end 10 and bottom end 20 can have identical construction.

For the illustrated application within a drug delivery pack, the spring 5 is preferably molded from polyethylene, polypropylene, Delrin™ and other plastic resins that are bio-compatible with sensitive drugs, reagents and other powders used in drug delivery applications. Preferably, the material is resilient and elastic to serve as the compression element of a drug delivery pack. The spring 5 is designed so that it can be readily injection molded, desirably with separate mold sections in the radial and axial planes of the spring, allowing extraction of the spring without damage to either the looped columns or the ribbed ends. Thus, the two sides and the two ends are desirably integrally molded together. Unlike a molded helical spring coil, no unwinding or special core pulls are required. The skilled artisan will readily appreciate numerous other materials and methods of construction (including compression molding, heat shaping, etc.), depending upon the desired characteristics of the spring.

Advantageously, the use of the alternating loop construction of the spring column(s) 40, 50 facilitates molding, as compared to coiled springs. Furthermore, the use of two (or more) columns, facilitates even pressure across the ends 10, 20, avoiding tipping of the ends 10, 20 relative the spring axis. In the illustrated context, this feature facilitates even pressure across a reagent bed, and thus even dissolution thereof.

Figure 2B:
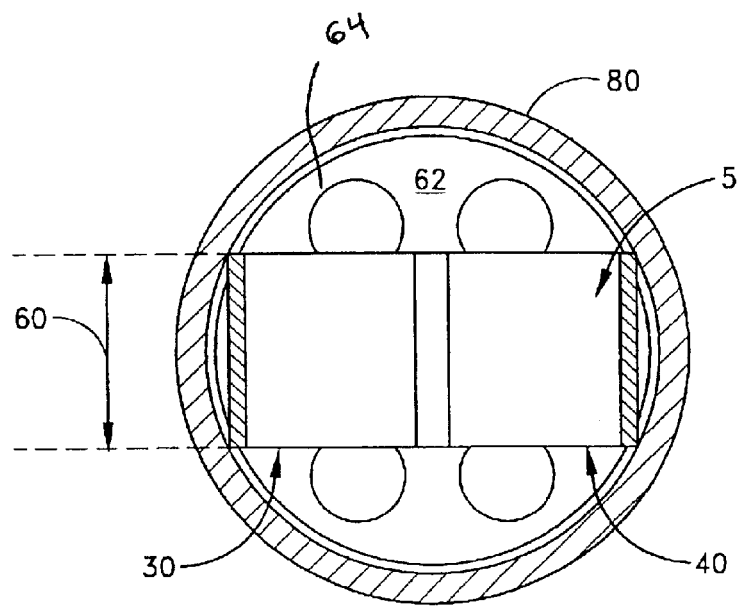
FIG. 2B is a cross sectional view taken along lines 2B—2B of FIG. 2A.
Figure 2A:
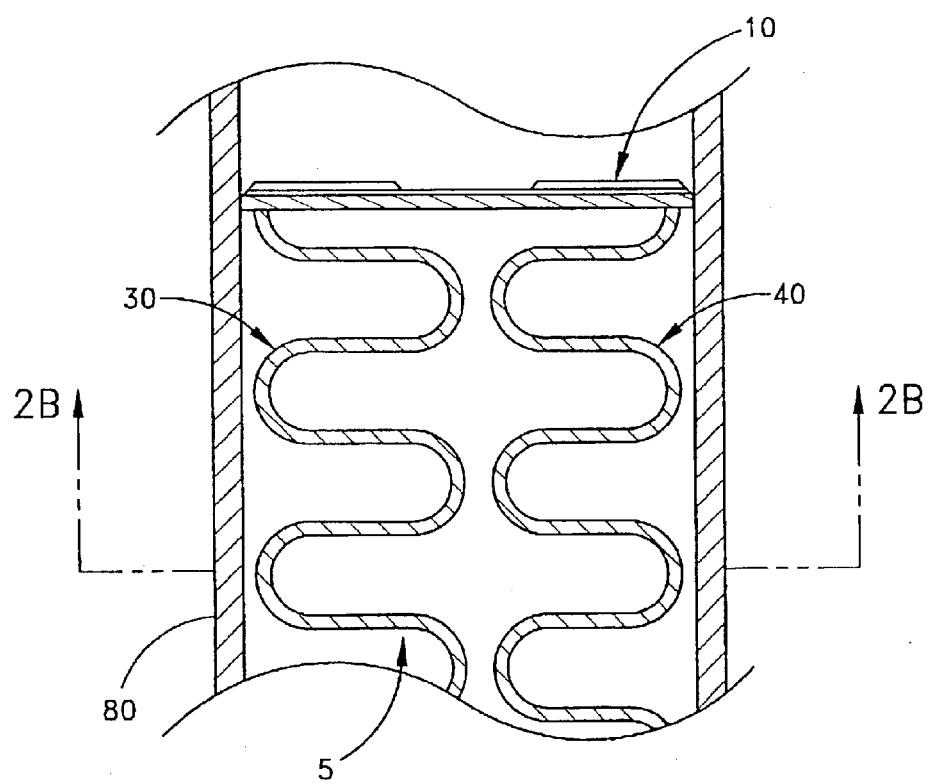
FIG. 2A is a partial elevational cross-section of the spring of FIG. 1 shown in relation to walls of a drug delivery pack housing.

With reference to FIG. 2A, the illustrated spring 5 is particularly constructed for fitting within a housing. A sidewall 80 of such a housing, preferably cylindrical, is shown in the drawings. The maximum width of the spring 5 is designed so that it matches the inner width of a housing within which the spring 5 is designed to be fitted. In particular, as best seen from FIG. 2A, the periphery of each end 10, 20 is designed to be equal to or slightly smaller than the housing sidewall 80, while the width of the fully compressed spring 5 (FIG. 1C) is equal to or slightly larger that of the ends 10, 20. Thus, the spring 5 self-centers within the housing defined by the sidewall 80.

The spring 5 is also designed to allow fluid flow through the housing in which it fits, despite the close fit of the spring 5 with the housing sidewall 80. In particular, the ribs 70 ensure that fluid flow is not blocked off when the spring ends 10, 20 mate with the corresponding ends (not shown) of the housing, and allow fluid flow distribution across the full inner width of the housing. The perforations 64 allow fluid flow into the housing through the top end 10 and out of the housing through the bottom end 20. As best seen from FIG. 2B, because the depth 60 of the columns 30, 40 is significantly less than the width of the housing, fluid readily flows in the housing around the spring 5, both when the spring 5 is at its free length as well as in the fully compressed (solid height) condition. Preferably, the depth 60 of the spring represents between about 10% and 90% of the housing diameter, and is about half the housing diameter in the illustrated embodiment.

Figure 3A:
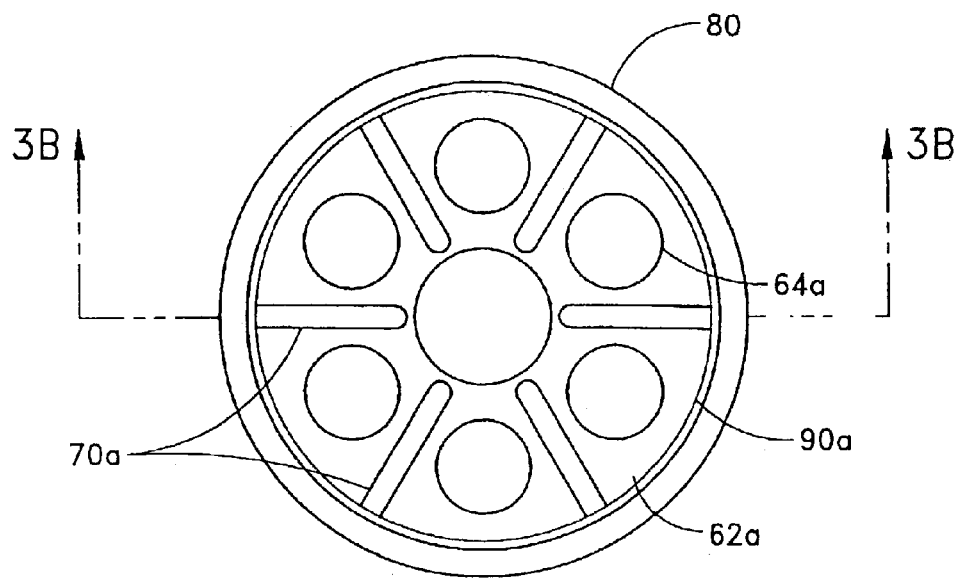
FIG. 3A is a top down view of a spring shown in relation to a drug delivery pack housing, constructed in accordance with another embodiment of the invention.
Figure 3B:
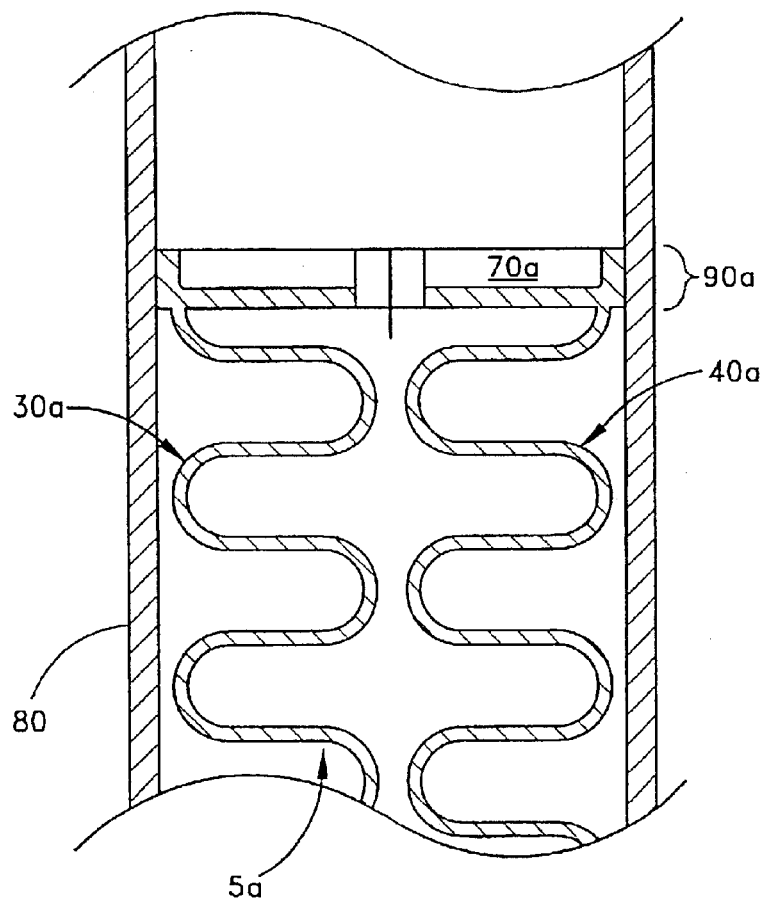
FIG. 3B is a partial, elevational cross-section taken along lines 3B—3B of FIG. 3A.

With reference to FIGS. 3A and 3B, a spring 5a is shown in accordance with another embodiment of the invention, wherein like parts are referenced by like numerals, with the addition of the prefix "a". In accordance with the illustrated embodiment, the ends 10a, 20a (top end 10a shown) of the spring 5a includes a peripheral collar 90a that extends axially from the edge of the platform 62a. For the illustrated circular end 10a, the collar 90a represents a short cylinder having an outer diameter approximately equal the inner diameter of the housing sidewall 80. The collar 90a further minimizes the potential for the spring ends 10a, 20a to tip during usage, since it tends to keep the top end 10a and the bottom end 20a level. As will be better understood in light of the discussion below regarding operation of the preferred drug reagent packs, the collar aids in keeping constant pressure across a reagent bed.

The skilled artisan will recognize other features and advantages of the illustrated spring for delivery pack or other applications, in view of the drawings and the description herein.

Plunger Design

The drug delivery packs or "reagent modules" of the '954 and '777 patents have numerous advantages, including the ability to store and easily transport drugs in a stable, dry form. Unfortunately, storage over extended periods of time can result in a loss of elasticity, reducing the effectiveness of the compression function. Many plastics, in particular, tend to set in the stored position over time due to a natural phenomenon with plastic resins known as "creep."

Figure 4:
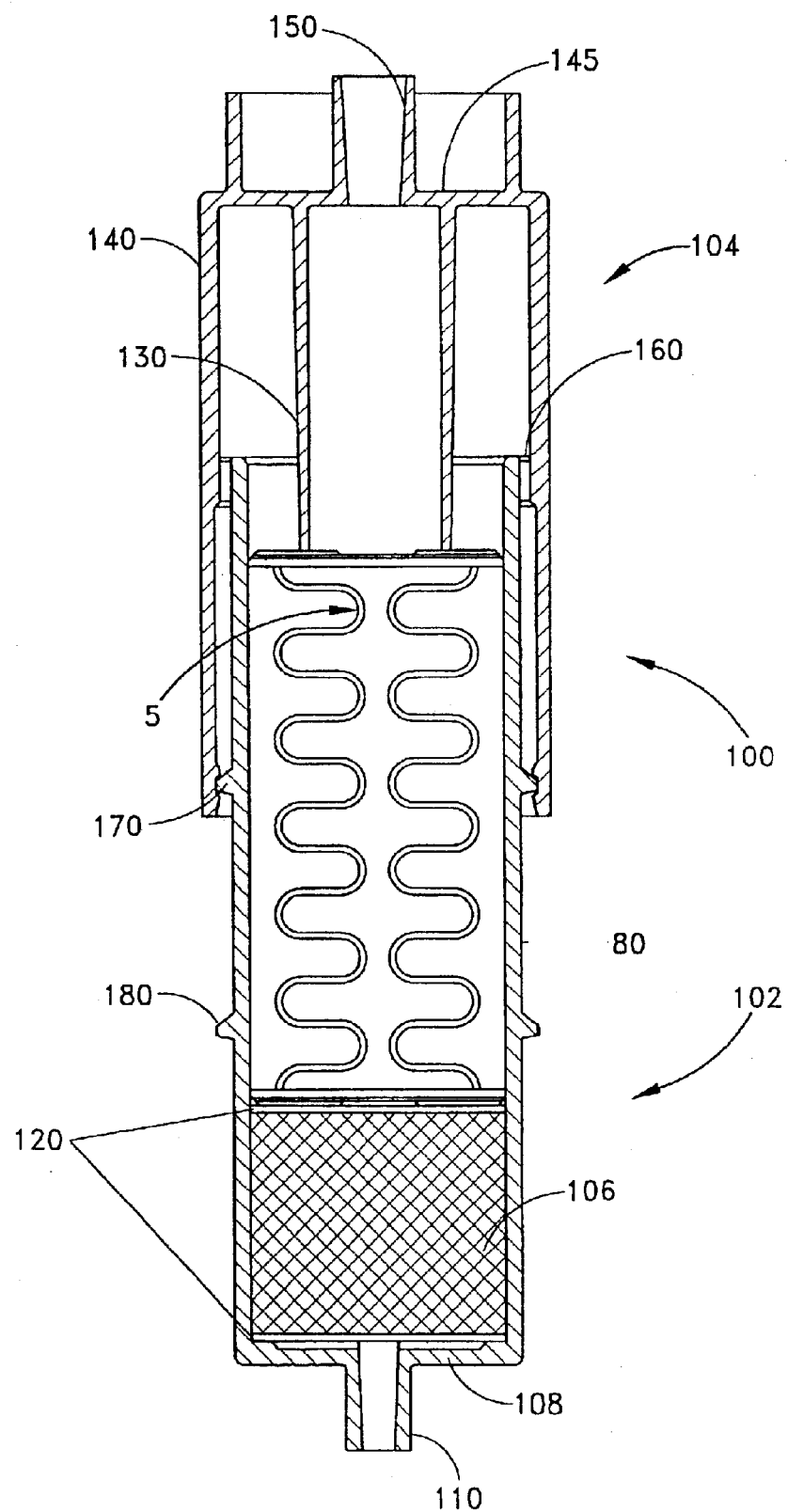
FIG. 4 illustrates a drug delivery pack incorporating the spring of FIG. 1 and a plunger mechanism, constructed in accordance with another embodiment of the invention.

Referring to FIG. 4, in order to better maintain elasticity and thus compression force of the spring over the storage life of a product, the present invention provides a drug delivery pack 100 having a sliding mechanism. The sliding mechanism is such that, at different positions, the compression component or spring 5 is compressed by different amounts from its free length. The slide mechanism is operated after assembly, such that the reagent and compression component is already enclosed by the housing. Accordingly, the drug delivery pack 100 can be packaged and shipped prior to compression of the spring 5 for operation. Desirably, the sliding mechanism ratchets or locks at at least a first position and at a second position.

In the illustrated drug delivery pack 100, the sliding mechanism is formed by a lower or inner housing portion 102 that fits coaxially with an upper or outer housing portion 104, the two portions being slidable relative to one another. The lower housing portion 102 is also referred to herein as a "spring housing" or "reagent housing" while the upper housing portion 104 is also referred to as a "top plunger."

The lower portion 102 includes the housing sidewall 80 (preferably cylindrical) and houses at least one reagent bed 106, preferably comprising a dry form of drug, buffering salt or other desirable constituent of a fluid to be formed. The reagent bed 106 is disposed above a housing floor 108 in which a bottom or outlet port 10 is formed, and the bed 106 is sandwiched between porous frits 120. Advantageously, the frits have a porosity that allows fluid carrying reagent (e.g., in solution form) to pass therethrough, but does not allow the dry particulates of the reagent bed 106 to pass therethrough. The lower portion 102 also houses a compression component arranged to exert pressure upon the reagent bed 106, desirably in the form of the novel spring 5 described hereinabove. While the illustrated embodiment includes one reagent bed, it will be understood that a plurality of such reagent beds can be provided within the same housing such that diluent flows sequentially therethrough. Such an arrangement is particularly advantageous for separately storing and reconstituting dry forms of incompatible reagents. More than one compression component can also be provided for multiple reagent beds.

The upper portion 104 includes an inner plunger 130, shown as a cylindrical wall or collar, and an outer sidewall 140 (preferably cylindrical) sized fit over the sidewall 80 of the lower portion. The plunger 130 depends from a housing ceiling 145 in which a top or inlet port 150 is formed.

The reagent pack 100 also includes features that facilitate temporarily locking the lower portion 102 to the upper portion 104 in at least two different positions representing different relative compressions of the spring 5. In the illustrated embodiment, the upper portion 104 includes, at the lower end of the cylindrical sidewall 140, an annular groove 152 defined by inwardly protruding ridges 154, best seen from the enlarged view of FIG. 7. The lower portion 102 includes, on the outer surface of the cylindrical sidewall 80, two vertically spaced rings 170 and 180 configured to mate with the groove 152 of the upper portion. The lower portion 102 also includes a small, flexible sealing lip 160 extending outwardly from the top of the cylindrical sidewall 80.

Figure 5A:
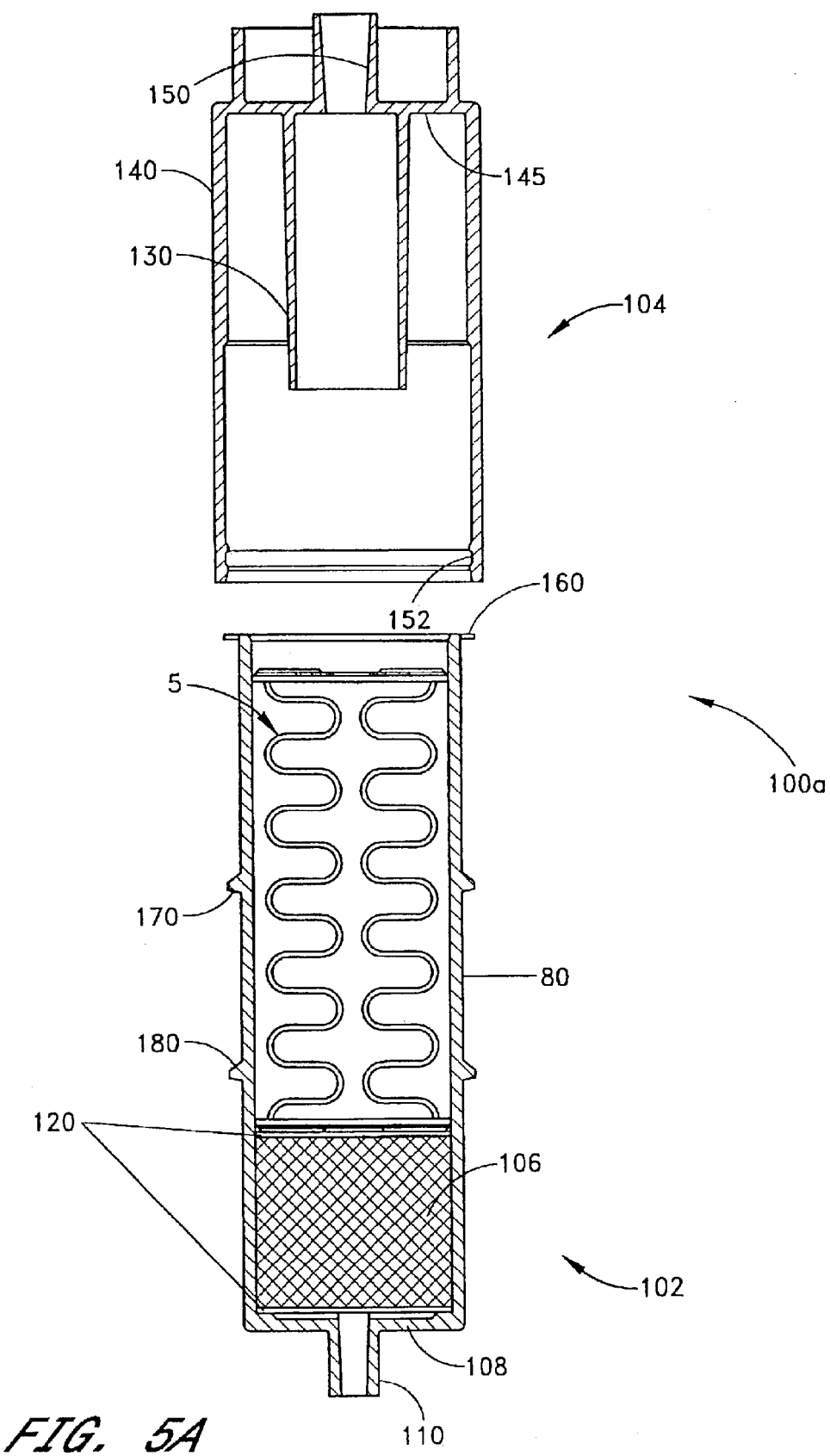
FIGS. 5A to 5C illustrate the drug delivery pack of FIG. 4 in unassembled (FIG. 5A), assembled (FIG. 5B), and cocked (FIG. 5C) conditions.
Figure 5B:
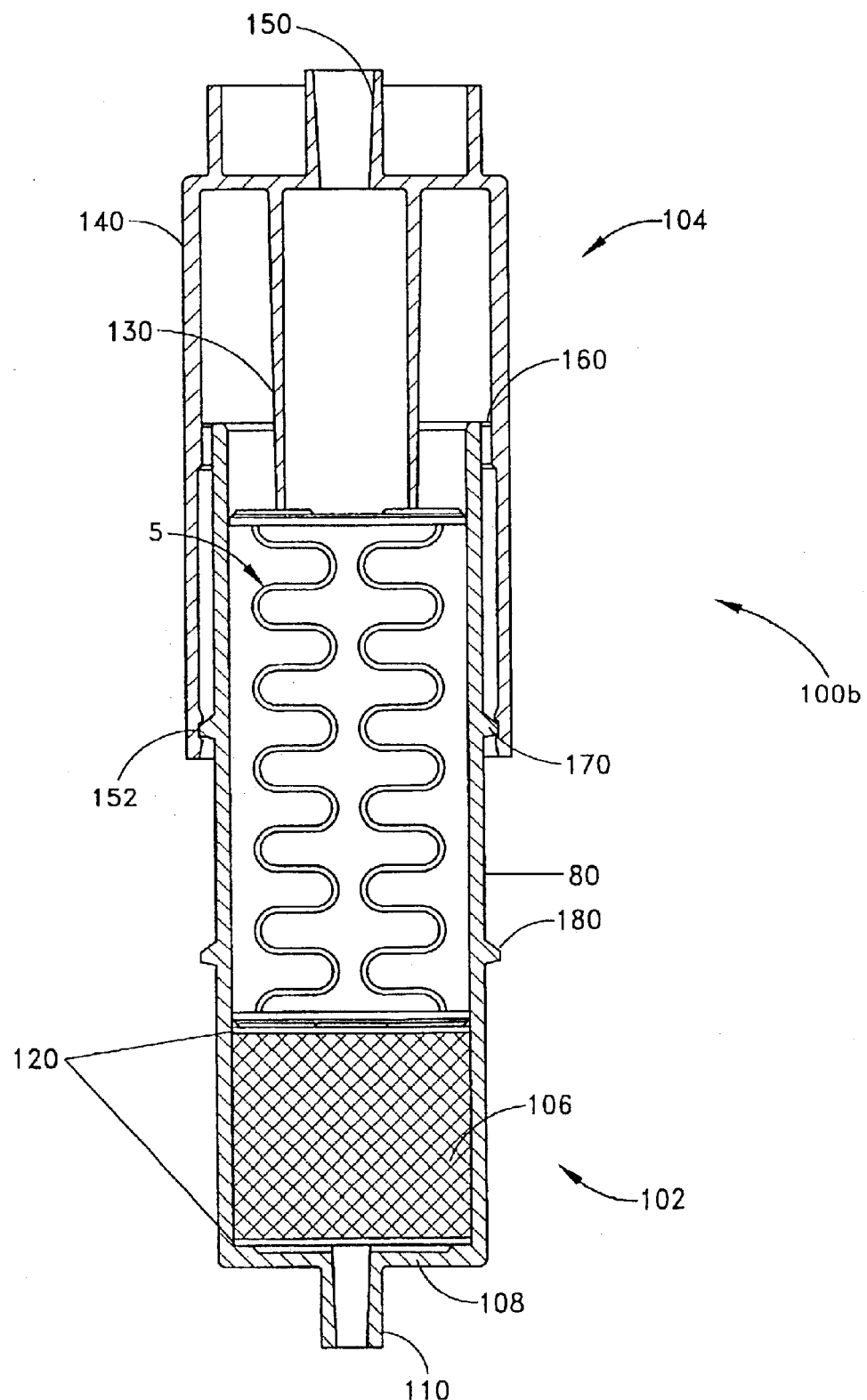
Figure 5C:
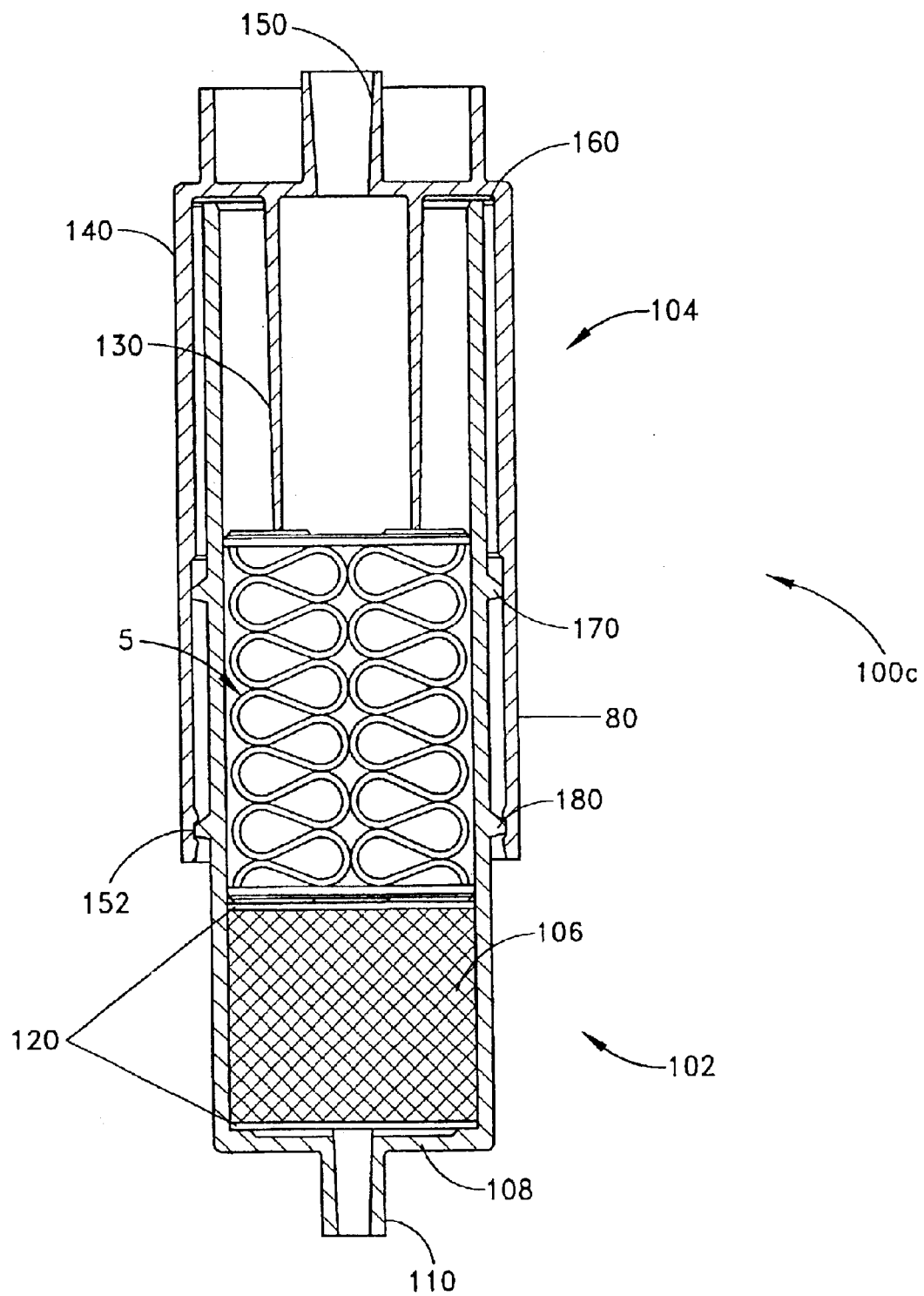

FIGS. 5A to 5C show the various stages of assembling and cocking the drug delivery pack 100.

Referring initially to FIG. 5A, prior to assembly, the plunger top 104 and reagent housing 102 of the unassembled drug delivery pack 100a are separate as shown. The reagent housing 102 is assembled by first placing the bottom frit 120 into the bottom. Then a suitable amount of reagent is added to form the reagent bed 106 and the top frit 120 is placed over the bed 106 to prevent escape of particulates from the bed 106. In accordance with one aspect of the invention, reagent can be loaded into the housing in liquid form, followed by in situ lyophilization. The spring 5 is inserted into the reagent housing 102 to rest on top of the top frit 120.

FIG. 5B shows the assembled drug delivery pack 100b after the plunger top 104 has been fitted over the reagent housing 102. As the reagent housing 102 is inserted into the plunger top 104, the sealing lip 160 of the reagent housing 102 contacts the bore of the plunger top 104, which has a smaller diameter than the sealing lip 160 diameter, causing the sealing lip 160 to deflect and seal against the sidewall 140 of the plunger top 104. The pack 100b is compressed such as by hand until the upper ring 170 of the reagent housing 102 snaps into the groove 152 of the plunger top 104. At the same time, the plunger 130 of the plunger top contacts the spring 5 and slightly compresses the spring 5.

Figure 7:
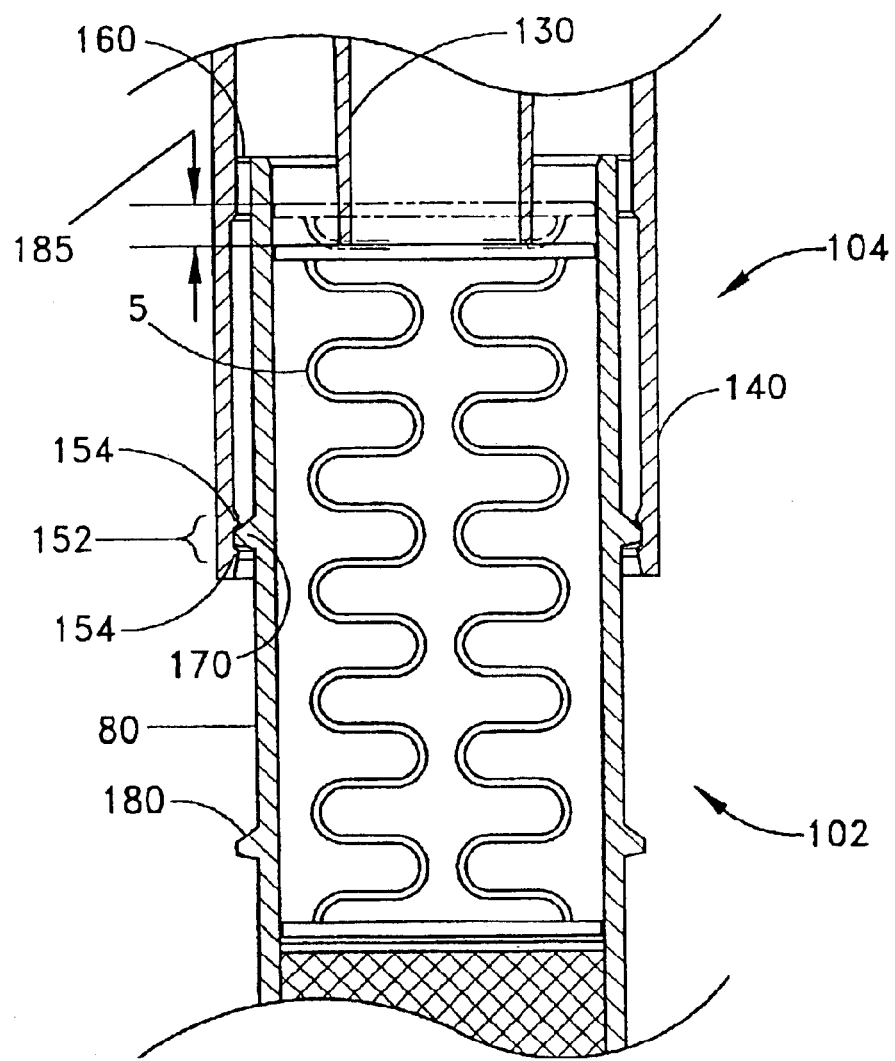
FIG. 7 is a detailed view of the assembled drug delivery pack of FIG. 5B.
Figure 8D:
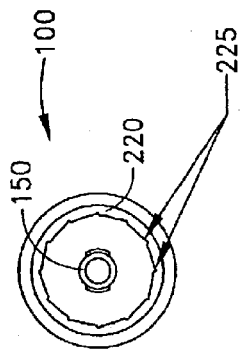
FIG. 8D is a top plan view showing an inlet portion of the drug delivery pack of FIG. 8C.
Figure 8C:
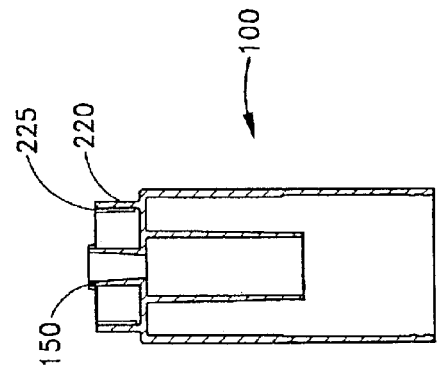
FIG. 8C is a partial, elevational cross-section of a drug delivery pack configured for mating with the water purification pack of FIG. 8A.
Figure 8B:
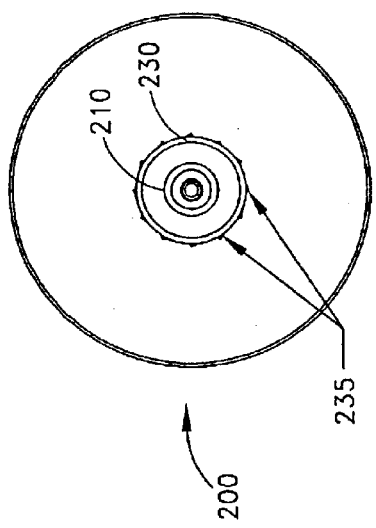
FIG. 8B is a bottom plan view showing an outlet portion of the water purification pack of FIG. 8A.
Figure 8A:
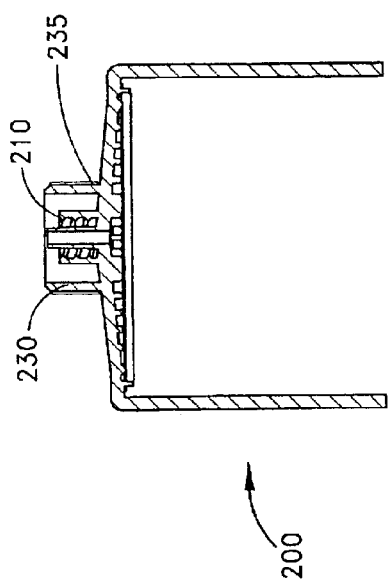
FIG. 8A is a partial, elevational cross-section of a water purification pack configured for irreversible locking with a preferred drug delivery pack.

FIG. 7 best shows the temporary interlocking of the reagent housing 102 with the plunger top 104 in the assembled condition. As shown, the groove 152 engages with the upper annular ring 170, at least with enough friction to oppose any expansive tendencies of the slightly compressed spring 5. The spring 5 is compressed by a distance 185, desirably just sufficient to prevent movement of parts within the assembled drug delivery pack 100b during shipping.

Referring again to FIG. 5B, the drug delivery pack is shipped and stored in this assembled configuration 100b until used by the consumer. In the assembled condition, the housing encloses the spring 5 and the reagent bed 106, though the enclosure is not necessarily sealed airtight. Preferably, however, the outlet port 110 and inlet port 150 are sealed, such as with caps (not shown) over conventional Luer connectors and/or foil seals. Preferably, the seals are applied prior to assembly. After assembly, the assembled pack 100b is packaged and shipped to the point of use.

FIG. 5C shows the cocked or loaded drug delivery pack 100c. Upon removal from the packaging and just prior to usage, the plunger top 104 is further compressed over the reagent housing 102. Sufficient force is applied to allow the upper ring 170 to unsnap from the groove 152. The plunger top 104 is pushed downward until the lower annular ring 180 of the reagent housing 102 snaps into the groove 152. The plunger 130 of the plunger top 104 further compresses the spring 5, such that the reagent bed 106 is under spring load. Advantageously, the distance between the upper ring 170 and the lower ring 180 is equal to or greater than the height of the reagent bed 106. Thus, the spring 5 can expand as reagent dissolves until the two frits 120 meet (see FIG. 13C).

In the illustrated embodiment, cocking the pack 100c involves sliding portions 102, 104 relative to one another in a manner that reduces the volume enclosed by the housing.

The skilled artisan will appreciate that, in other arrangements, a separate sliding mechanism or plunger can be provided to load the compression component without changing the volume enclosed by the housing.

The illustrated drug delivery device allows controlled compression of a powder or drug during dissolution, as disclosed in the '954 and '777 patents, while avoiding the creep problem mentioned above. The illustrated device is particularly advantageous with a plastic spring 5. The spring 5 is kept in a relatively relaxed assembled condition 100b (not under load) during normal shelf life of the product, as shown in FIG. 5B—storage and handling conditions that can last over a year, depending upon the shelf life of the particular drug or other powdered reagent. Once ready for usage, the spring 5 is compressed in a cocked or loaded condition 100c, as shown in FIG. 5C, and used within a short period of time, thus avoiding creep or spring set usually associated with a compressed spring over time.

Figure 6:
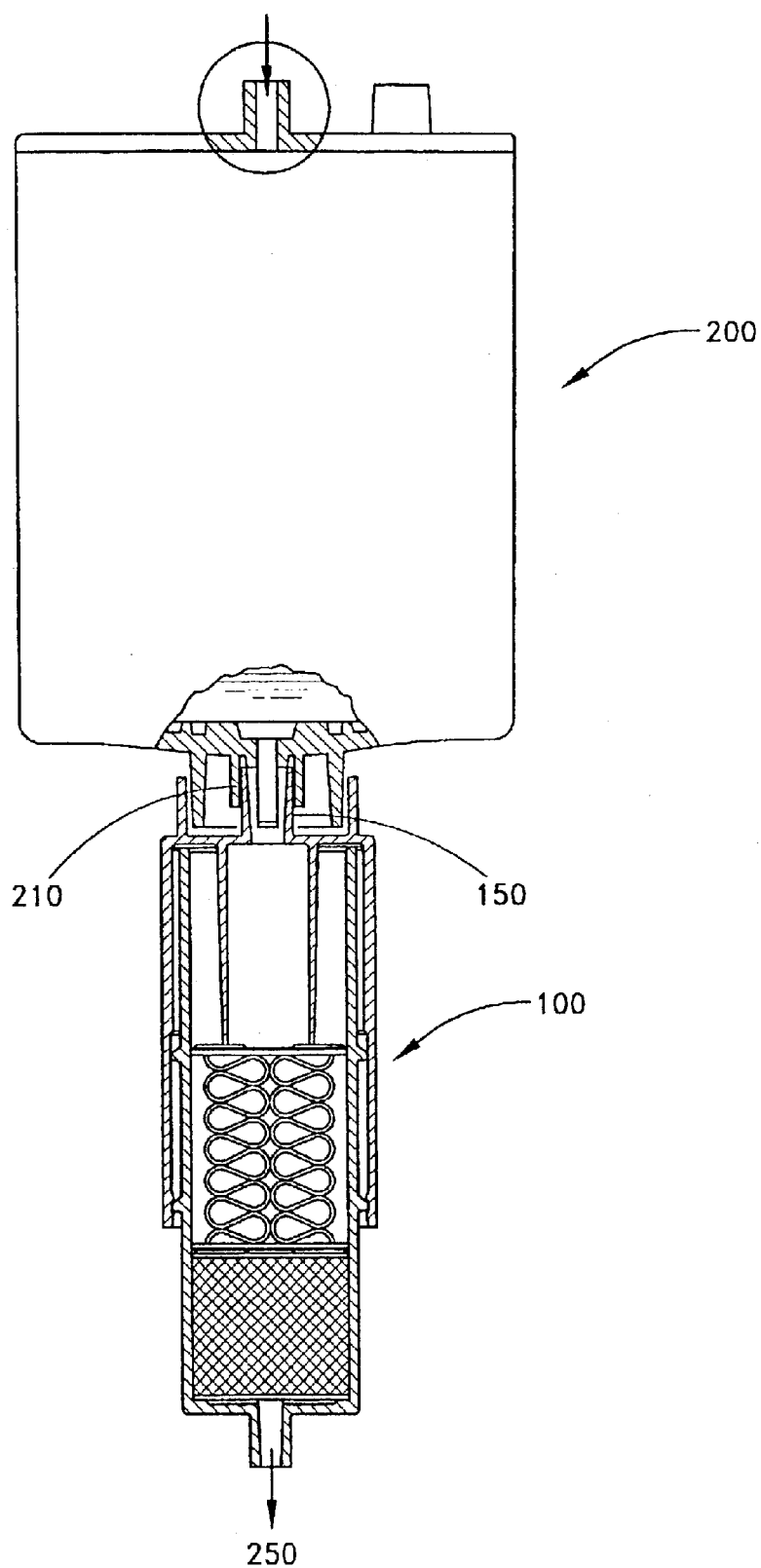
FIG. 6 illustrates the cocked drug delivery pack of FIG. 5C in connection with a water purification pack.

With reference to FIG. 6, a diluent source 200 is shown attached to the upstream or inlet port 150 of the assembled and cocked drug delivery pack 100. The diluent source 200 can comprise any suitable reservoir of sterile diluent, such as a bag of sterile saline. Preferably, the diluent source 200 comprises a water purification pack that purifies non-sterile water as it flows therethrough, such as that disclosed in the '954 and '777 patents. More preferably, the diluent source comprises a water purification pack as disclosed in U.S. patent application Ser. No. 09/364,631, filed Jul. 30, 1999 and entitled IMPROVED WATER PURIFICATION PACK, the disclosure of which is expressly incorporated herein by reference. The downstream end of the diluent source 200 can be connected in any suitable fashion, such as by standard Luer lock connections, as shown in FIG. 6. In particular, the drug delivery device inlet port 150 includes a standard male Luer lock connector, and a diluent source outlet port 210 includes a standard female Luer lock connector.

Referring to FIGS. 8A to 8D, in one embodiment, the connection between the diluent source 200 and drug delivery pack 100 is irreversible. As used herein, "irreversible" connection means that if the diluent source 200 and drug delivery pack 100 were separated, the features allowing connection would be so damaged as to render re-use impractical. Accordingly, the irreversible connection is designed to permit only one-time use of the drug delivery pack, such that partial doses or refilled reagents could not be delivered after the sterility of the device has been compromised. As will be appreciated by the skilled artisan, irreversible connection of any device, tube, etc., to either the inlet or outlet sides of the drug delivery device, will accomplish the same goal.

In the illustrated embodiment, the connection includes the standard Luer lock connection between the inlet port 150 of the drug delivery pack 100 and the outlet port 210 of the diluent source 200, as discussed with respect to FIG. 6. Additionally, however, the drug delivery pack 100 has a collar 220 coaxially surrounding the inlet port 150, having vertical ratchet teeth 225 on an inside surface thereof. The diluent source 200 includes a mating collar 230 configured to fit within the collar of the drug deliver pack 100. The mating collar 230 includes mating ratchet teeth 235.

Figure 9:
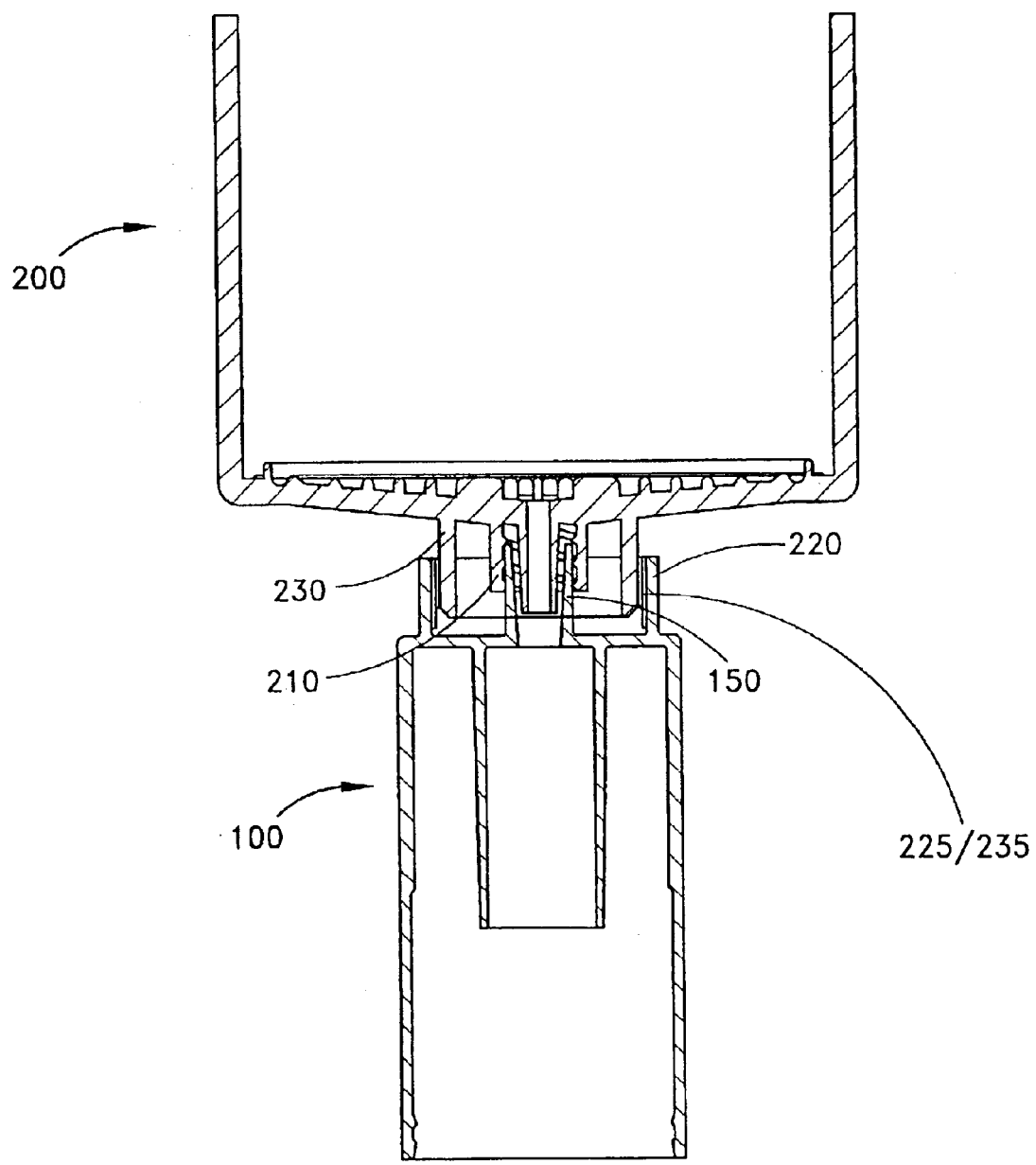
FIG. 9 illustrates the drug delivery pack and water purification pack of FIGS. 8A to 8D in an irreversibly engaged condition.

Referring to FIG. 9, when the devices 100, 200 are fitted together and twisted to engage the Luer lock components 150, 210, the ratchet teeth 225, 235 interact to permit rotation that engages the Luer lock components but do not allow rotation to disengage the Luer lock connectors. Once engaged, the drug delivery pack cannot be readily removed from the diluent source 200 without visible or functional damage to the connectors. Accordingly, the drug delivery device 100 is unlikely to be reused accidentally or even intentionally.

By-pass Mechanism

FIGS. 10 to 14C illustrate another improvement over the drug delivery devices of the '954 and '777 patents. In particular, mechanisms and methods are provided herein for establishing an initial flow of diluent that by-passes the reagent bed. The initial flow of diluent is particularly advantageous for priming the drug delivery device for establishing a consistent drip rate prior to activation of the drug delivery device, as will be understood from the disclosure herein.

Figure 10:
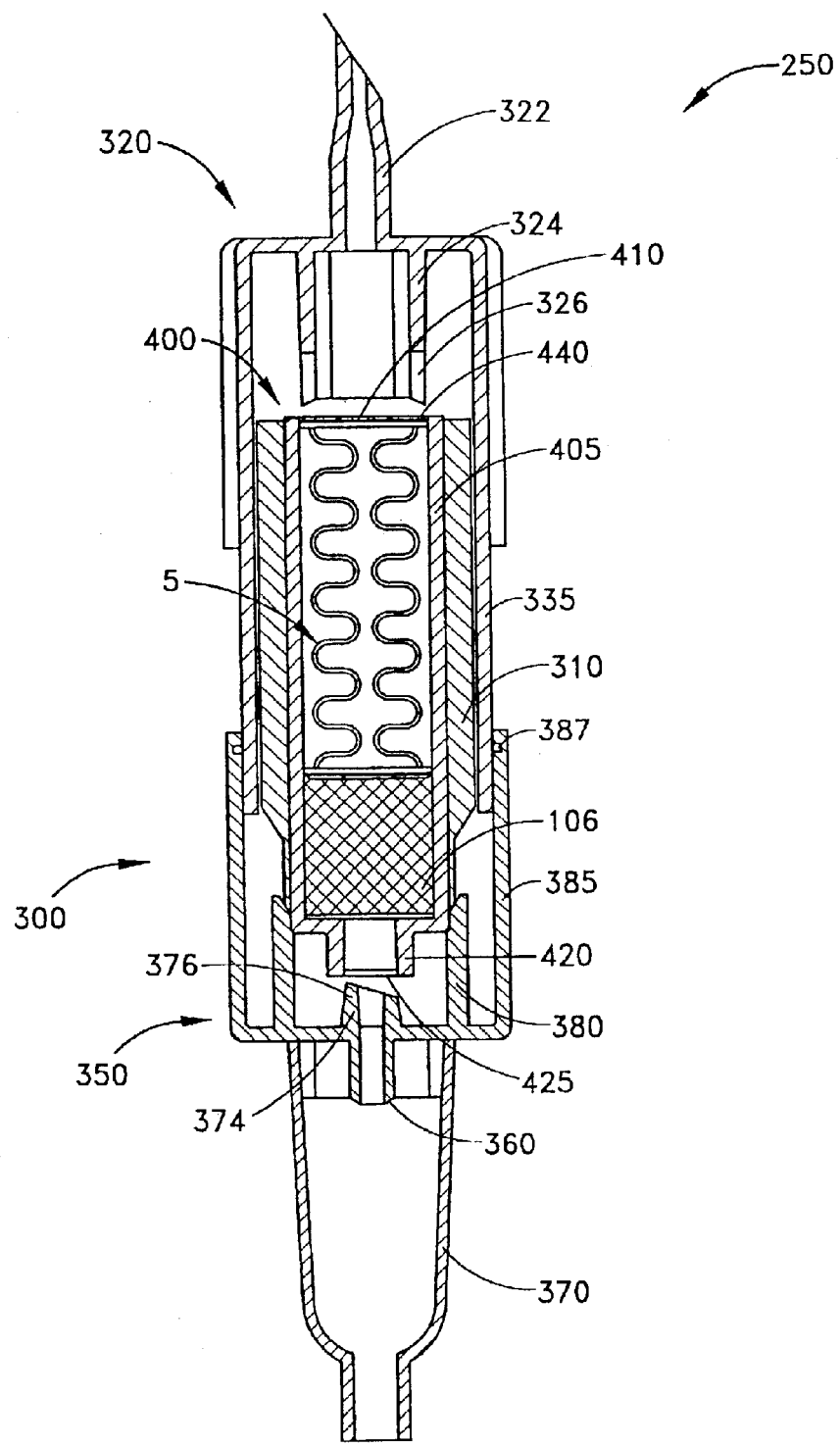
FIG. 10 is a cross-sectional view of a drug delivery pack constructed in accordance with another embodiment of the invention.
Figure 12:
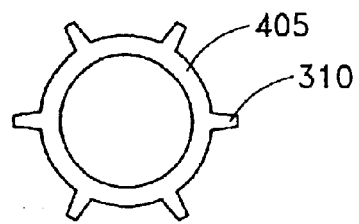
FIG. 12 is an end view of a ribbed outer wall of the capsule in FIG. 11.
Figure 11:
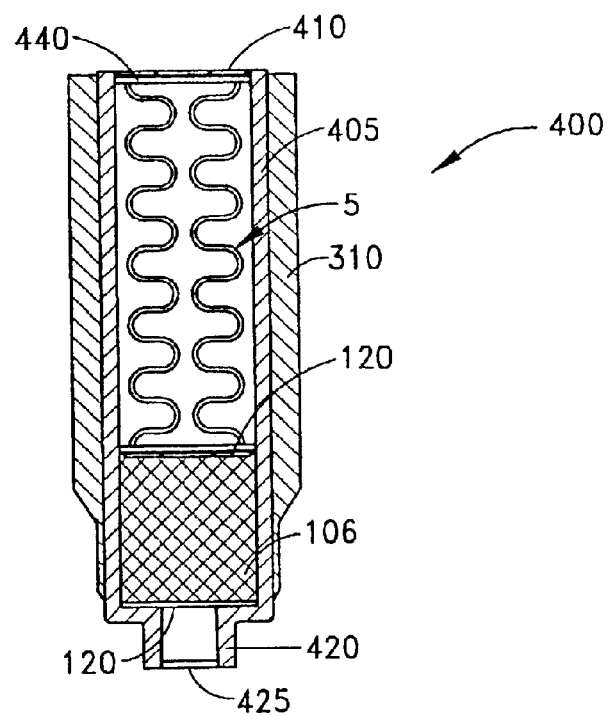
FIG. 11 is a cross-section of a drug capsule portion of the drug delivery pack of FIG. 10.

Referring initially to FIGS. 10–12, a drug delivery device 250 of the illustrated embodiment comprises a housing 300 and a sealed a reagent capsule 400 surrounded or enclosed by the housing 300. Desirably, the reagent capsule 400 includes a plurality of spacers, illustrated in the form of axially elongated ribs 310, along the outer surface thereof. The housing 300 comprises a two-piece sliding mechanism, similar to the plunger mechanism previously described. In a first or assembled configuration, the reagent capsule is surrounded by the housing 300 but is arranged to allow diluent flow within the housing but outside the reagent capsule 400, desirably along a flow path defined by the spacers (ribs 310) between the housing inner surface and reagent capsule 400. In a second or primed configuration, the housing 300 is compacted and shifts the diluent flow path such that diluent flows exclusively through the reagent capsule 400, eroding the reagent bed and carrying reagent with it as it flows.

Referring to FIG. 10, in the first preferred embodiment, the housing 300 comprises an upper housing portion 320 and a lower housing portion 350. Unlike the previously described embodiment, the upper housing portion 320 fits within the lower housing portion 350, though it will be understood that this arrangement can be readily reversed.

The upper housing portion 320 includes an inlet port 322 at an axial upper end. While shown in the form of a bag spike for accessing diluent from a sterile bag, it will be understood that, in other arrangements, the inlet can take the form of a standard Luer lock connector, as described for the previous embodiment. The inlet port 322 extends downstream into an inlet or plunger collar 324, the downstream or distal end of which is sharpened into a piercing member 326. The upper housing portion 320 also includes an axially extending outer cylindrical sidewall 335 sized to receive the maximum outer width of the reagent capsule 400, with is defined by the ribs 310. Though not shown, it will be understood that the sidewall 335 also includes at least two annular rings protruding from the outer surface thereof, facilitating snap-fit into a correspond groove on the inner surface of the lower housing portion 350 for an assembled configuration and a cocked configuration.

The lower housing portion 350 includes an outlet port 360 at an axial lower end. Downstream of the outlet is a drip chamber 370 for collecting diluent and reagent. The skilled artisan will appreciate that the drip chamber 370 allows for a metered delivery of dissolved or suspended reagent, as desired for many intravenous (IV) applications. Advantageously, the drip chamber 370 is formed of a flexible material, such as vinyl, such that the chamber can be squeezed to vent lines prior to activation of the drug delivery pack 250. The drip chamber 370 can be separately or integrally provided. It will be understood that, in assembly prior to use, an integral drip chamber 370 would be capped to maintain sterility. The outlet port 360 extends upstream into an outlet collar 374, the upper end of which is sharpened into a lower piercing member 376. The outlet collar 374 is sized to be received within an outlet of the reagent capsule 400, as described below. The outlet collar 374 is surrounded by a plurality of support columns 380. In the illustrated embodiment, the support columns 380 comprise four arcuate posts, forming a discontinuous cylinder with openings at 90° to one another. The discontinuities serve to provide fluid flow paths during priming and to permit outward deflection during cocking, as described below. The lower housing portion 350 further includes an axially extending cylindrical sidewall 385, sized to receive the sidewall 335 of the upper housing portion 320. The sidewall 385 includes on an inner surface thereof a groove 387 arranged to receive the annular rings of the upper housing portion 320 in a snap-fit relation.

Referring to FIG. 12, the reagent capsule 400 comprises a cylindrical sidewall 405 with the described spacers in the form of elongated ribs 310 extending integrally outward therefrom. An upstream reagent seal 410 extends across an upstream end of the sidewall 405. The downstream end of the reagent capsule 400 terminates in a reagent outlet collar 420, across which a downstream seal 425 preferably extends. The reagent capsule 400 houses a reagent bed 106 sandwiched between two frits 120, and having an adjacent compression component, preferably in the form of the polymeric spring 5. In the illustrated embodiment, these elements can be similar to the corresponding elements of the previously described embodiment, such that like numbers refer to like parts. Desirably, the reagent bed 106 and spring 5 are loaded into the reagent capsule, the spring is slightly pre-loaded (see FIGS. 5B and 7 and accompanying description) to prevent shifting of parts during transport, and the seals 410, 425 are applied prior to assembly.

The seals 410, 425 are desirably resistant to the passage of diluent. They can comprise foils or suitable hydrophobic barriers such as polymeric sheets or laminates. Exemplary hydrophobic polymers includes polypropylene, PVDF (polyvinylidene difluoride), and acrylic copolymer. These and other polymers can be treated in order to obtain specific surface characteristics that can be both hydrophobic and oleophobic (repelling liquids with low surface tensions, such as multivitamin infusions, lipids, surfactants, oils, and organic solvents). Another property of the hydrophobic barrier 410 is that it allows air to flow through it.

The housing 300 and reagent capsule 12 are assembled to form the assembled drug delivery pack 250 shown in FIG. 10. Prior to the process of FIGS. 13A to 13C, the drug delivery pack 250 is assembled by inserting the reagent capsule 400 within the upper housing portion 320, and inserting both of these units within the lower housing portion 350. The housing portions 320, 350 are compacted together, with the upper portion 320 sliding within the lower portion 350 until the groove and first ring snap together. The inlet port 322 of the assembled housing 300 and the outlet port 360 (and/or the outlet of the drip chamber 370) are preferably provided with caps or port covers (not shown) to maintain sterility. The device can be packaged, shipped and stored in this form until ready for use.

Figure 13A:
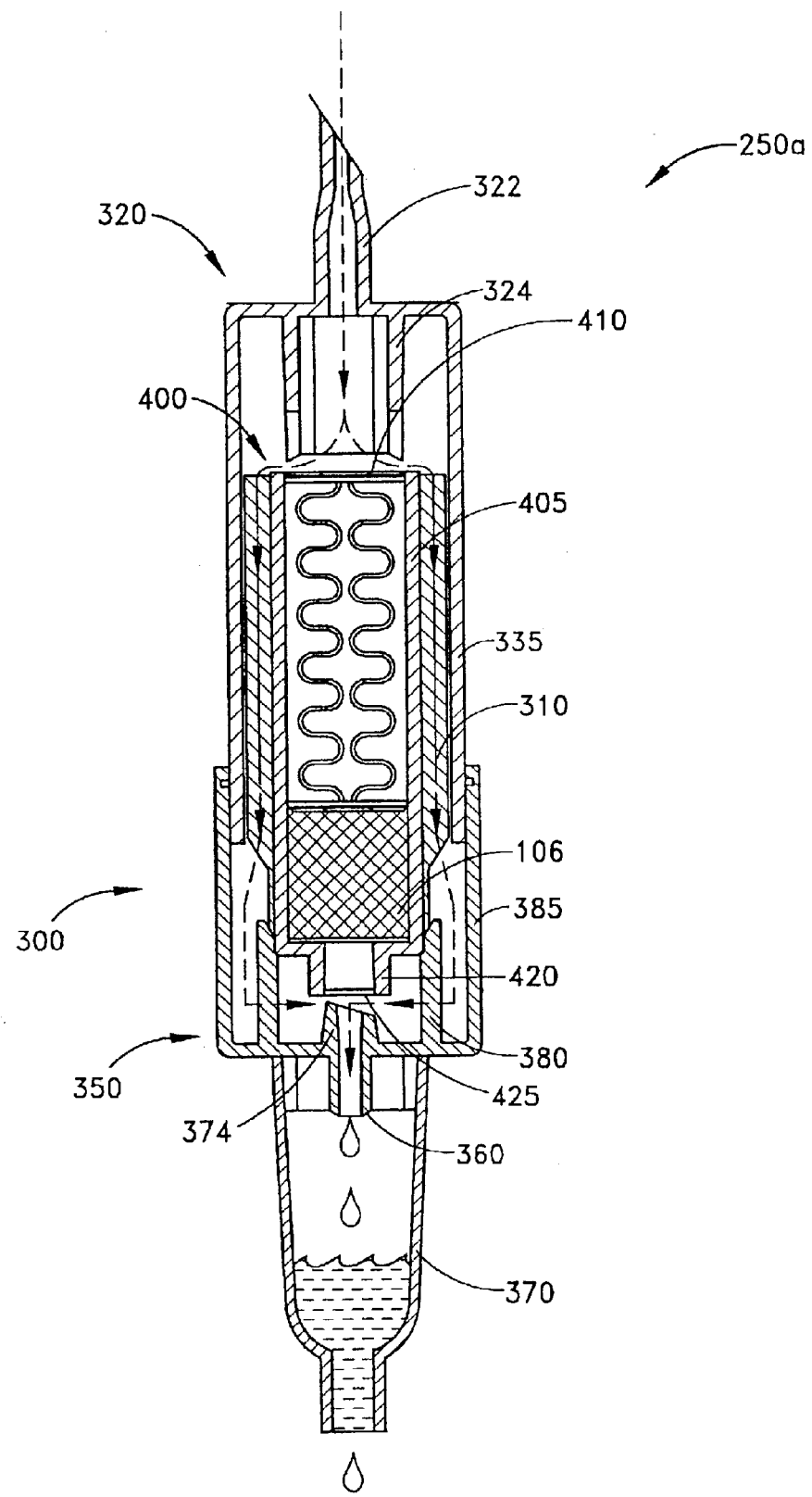
FIG. 13A is schematic cross-section, similar to that of FIG. 10, illustrating water flow within the drug delivery pack but outside the drug capsule during a priming stage.
Figure 13B:
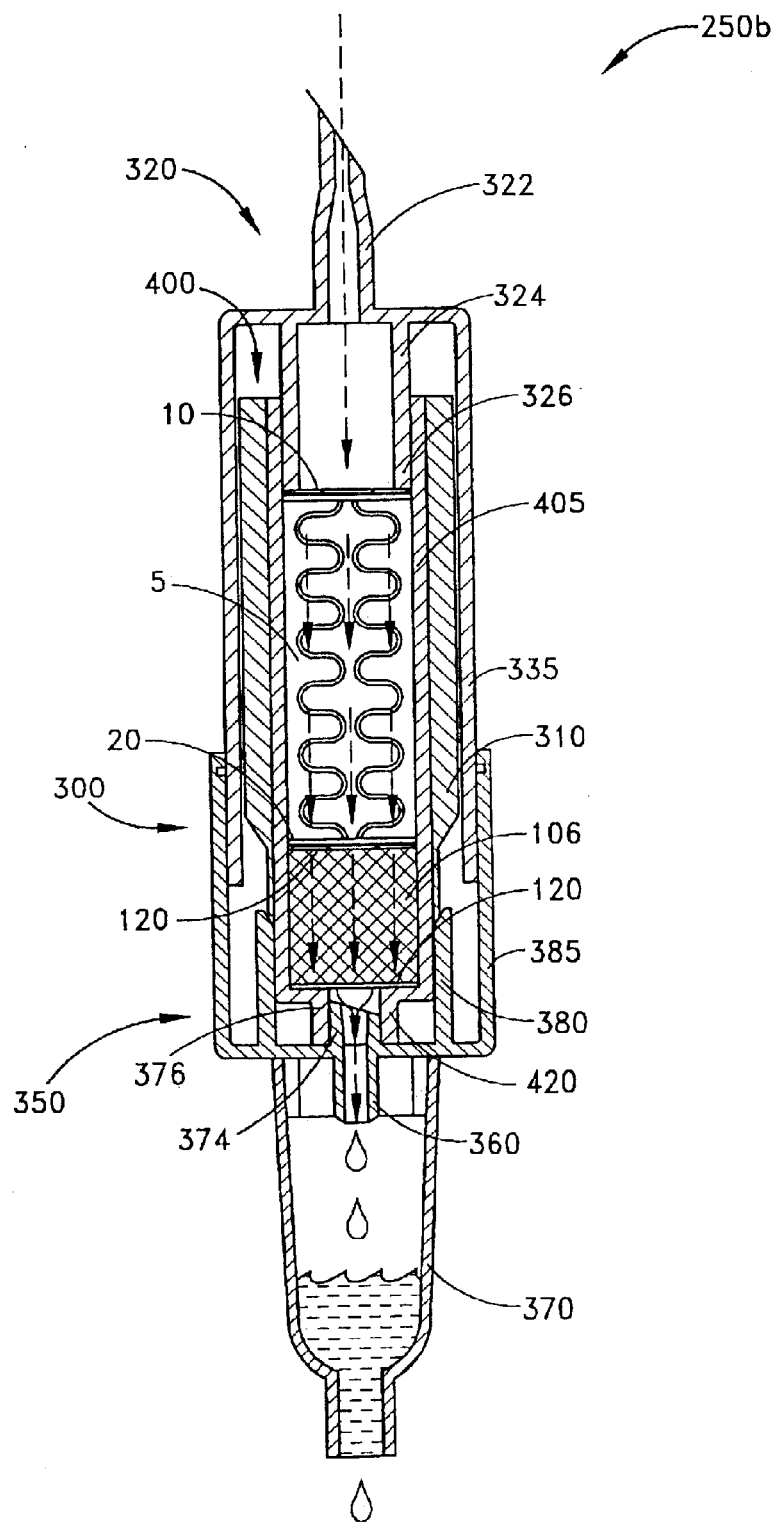
FIG. 13B illustrate the drug deliver pack of FIG. 13A after priming and during compression to cock the pack and initiate drug delivery.
Figure 13C:
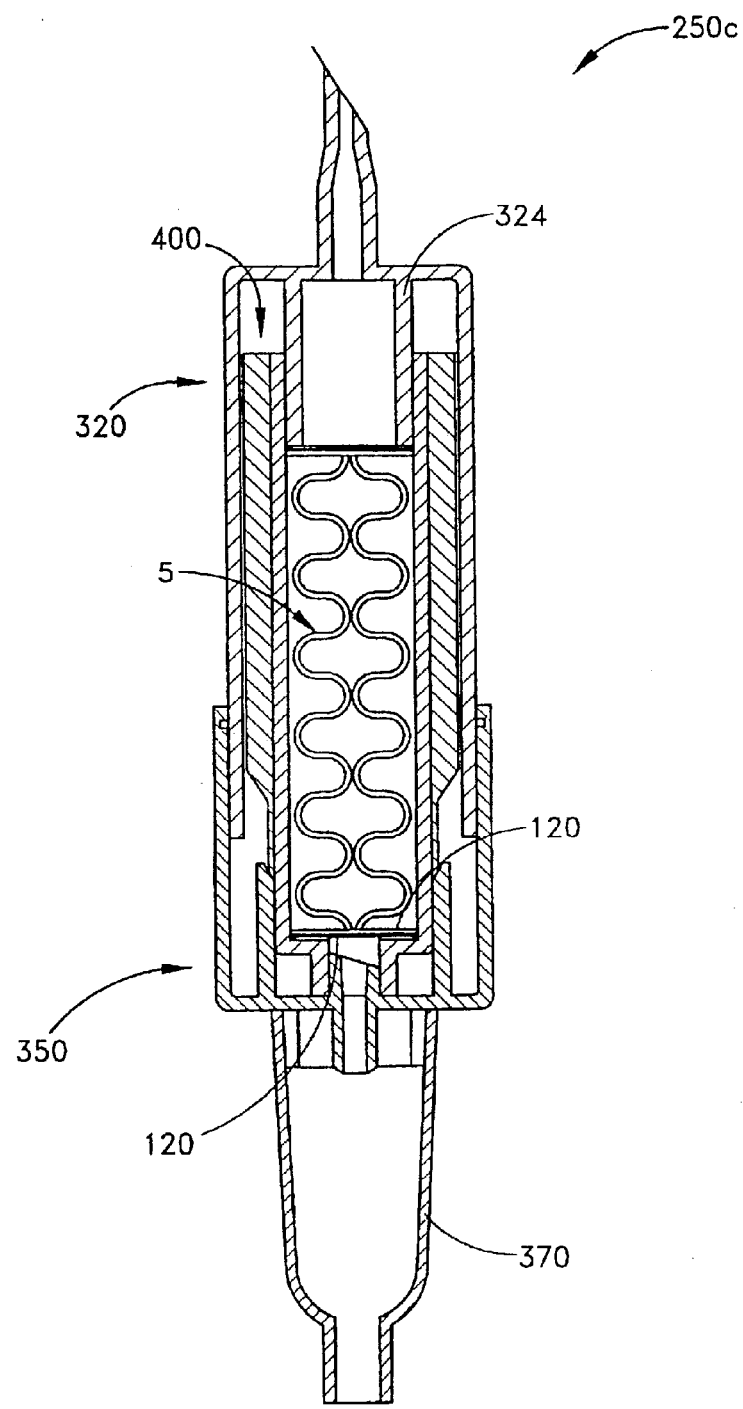
FIG. 13C illustrates the drug delivery pack of FIG. 13B after the reagent bed has been fully discharged.

With reference to FIGS. 13A to 13C, the operation of the drug delivery device 250 and its by-pass mechanism is shown.

Initially referring to FIG. 13A, the assembled drug delivery pack 250a is primed for operation by initiating diluent flow through the pack 250a. Arrows show the direction of fluid flow in the drawings. Diluent first enters the inlet port 322 and through the cavity defined by the inlet or plunger collar 324. In the illustrated embodiment, this involve piercing a diluent reservoir with the spike of the inlet port 322, though the skilled artisan will readily appreciate numerous alternative diluent sources and connectors. The reagent capsule upstream seal 410 prevents diluent from entering the reagent capsule 400. Accordingly, diluent flows along a by-pass path provided by the annular space between the housing 300 and the reagent capsule 400. In particular, the elongated ribs 310 provide channels in the space between the reagent capsule sidewall 405 and the upper housing portion sidewall 335. The diluent continues downstream though gaps or discontinuities among the support columns 380 that surround the outlet collar 374, through the collar 374, though the outlet port 360 and into the drip chamber 370. Squeezing the drip chamber expels air from the pack 250a and establishes a drip rate for the device.

Referring to FIG. 13B, the cocked or activated drug deliver pack 250b is formed by compacting the housing 300 around the reagent capsule 400. Applying hand pressure, for example, to the top of the upper housing portion 320 and the bottom of the lower housing portion 350 closes off the by-pass flow path. In particular, the reagent capsule 400 is forced downward relative to the lower housing portion 350, such that the reagent outlet collar 420 fits over and surrounds the outlet collar 374 of the lower housing portion 350. The sharpened ends 376 of the outlet collar 374 pierce or rupture any downstream seal 425 (FIG. 13A) over the reagent outlet collar 420, opening fluid communication between the reagent capsule 400 and the outlet port 360. Similarly, the upper housing portion 320 is forced downward relative to the reagent capsule 400, such that the inlet or plunger collar 324 slides within and is surrounded by the sidewall 405 of the reagent capsule 400, cutting off fluid communication between the inlet port 322 and the by-pass flow path. The sharpened ends 326 of the plunger collar 324 pierce the upstream seal 410, opening fluid communication between the inlet port 322 and the reagent capsule 400. The plunger collar 324 also preferably charges the spring 5 by pushing down on the top end 10 thereof.

Diluent continues to flow, entering the reagent capsule 400 through the perforated top end 10 of the spring 5, around the spring 5, through the perforated bottom end 20 of the spring 5, through the upstream frit 120, the reagent bed 106 and the downstream frit 120. As the diluent flows through the reagent bed 106, the bed is eroded, such as by dissolution into the flowing diluent, and the reagent-carrying fluid continues past the downstream frit 120, through the reagent outlet collar 420, through the housing outlet 360 and into the illustrated drip chamber 370. The skilled artisan will appreciate that, in other arrangements, the reagent-carrying fluid (e.g., solution) can be delivered directly to a collection reservoir for use as a standard medical fluid soon thereafter. As the reagent bed 106 is eroded, the compression component (spring 5) continues to compact the bed 106 to prevent erosion channels from forming therein. An even rate of dissolution is thus obtained until the reagent bed 106 is completely or substantially consumed.

Referring to FIG. 13C, the expended or spent drug delivery pack 250c is shown after all of the reagent bed 106 (FIG. 13B) has been consumed. As shown, the spring 5 has fully expanded during the process until the upstream and downstream frits 120 that had sandwiched the reagent bed 106 meet. Desirably, the housing sidewalls 335, 385, 405 of each component are made substantially transparent, such that an operator can visualize delivery of the reagent from the bed into the flowing diluent and the completion of the process. Failure to deliver a full does would thus be easily detected.

Lyophilization within the Drug Delivery Pack

Figure 14:
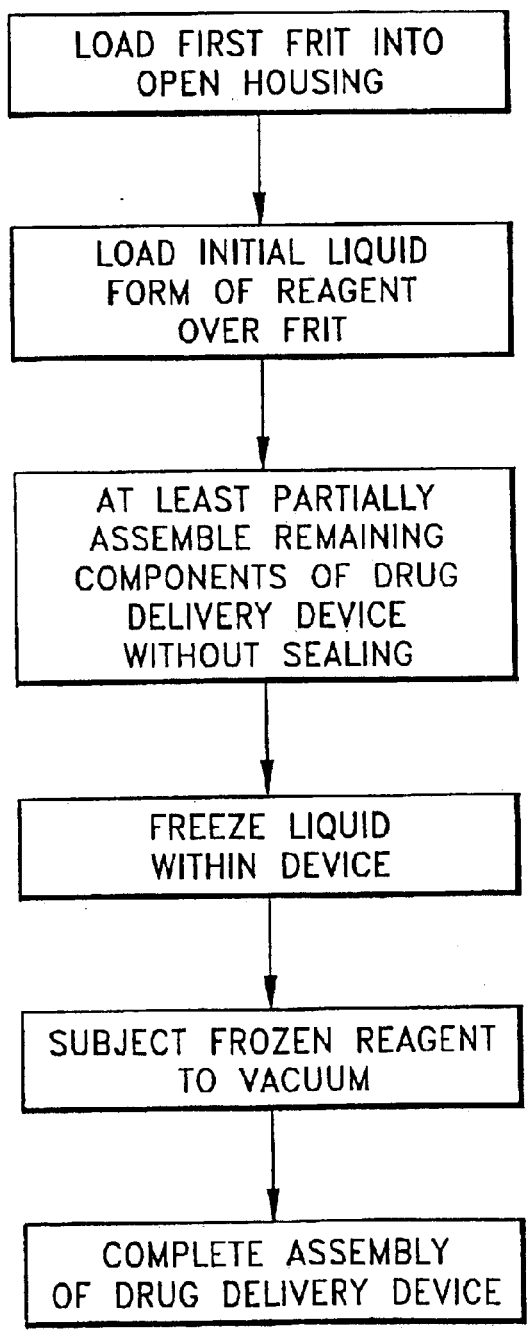
FIG. 14 is a flow chart illustrating a process of lyophilizing reagents within the drug delivery packs of the preferred embodiments.

FIG. 14 illustrates a method of forming a dry reagent bed within a drug delivery device, in accordance with another embodiment of the present invention. Though the method is not exclusive to them, the above-described drug delivery packs 100, 250 are particularly advantageous for implementing the method. Accordingly, the method will be described with reference to drug delivery pack 100 of FIGS. 4 to 7.

The preferred embodiment begins with the unassembled drug delivery pack 100a (FIG. 5A) prior to loading frits 120, reagent and compression component (spring 5). As shown in FIG. 14, the lower or downstream frit 120 is first loaded 500 into the lower housing portion 102. The frit 120 preferably comprises a hydrophobic material that will support a fluid thereupon, yet is permeable to air and vapors. An exemplary frit is a multilayered polypropylene laminate, having a porosity between about 1 $\mu$m and 100 $\mu$m, more preferably between about 10 $\mu$m to 50 $\mu$m. Further details on the preferred material are given below, with respect to the reagent restraints.

An initial liquid form of the reagent to be lyophilized is then loaded 510 into lower housing portion 102 over the lower frit 120. Note that the initial liquid form need not have the same concentration or diluent as ultimately formed upon delivery. Rather, the initial liquid form is preferably more concentrated than that desired for delivery, and is most preferably as concentrated as possible without having the reagent fall out of solution and lower yield.

The remaining components of the drug delivery device are then at least partially assembled 520. For the illustrated pack 100, this involves inserting the upper or upstream frit 120 over the initial liquid form of the reagent, followed by the spring 5 and the upper housing portion 104. It will be understood that some of these components can alternatively be loaded prior to loading 510 the initial liquid form of the reagent; for example, in another arrangement the compression component can be positioned downstream of the reagent bed.

The pack 100 is left unsealed at this point. Preferably at least one of and more preferably both of the inlet port 150 and the outlet port 110 are left uncovered at this stage of the process. Moreover, the "partially assembled" drug delivery pack 100 is preferably not closed off, unlike the pack 100b of FIG. 5B. Rather, "partial assembly" in the sense of FIG. 14 means only that the components are sufficiently assembled to bring slight pressure to bear on the initial liquid form of reagent sandwiched between the frits 120. In the illustrated embodiment, the inner plunger 130 of the upper housing portion 104 is allowed to rest under gravitational force on the spring 5, but the upper housing portion 104 is preferably not compacted under force enough to catch the groove 152 upon the first annular ring 170. Accordingly, the sealing lip 160 does not quite reach the thick upper section of the upper portion sidewall 140 and therefore does not form a seal between the upper housing portion 104 and the lower housing portion 102. While the most preferred arrangement thus leaves three potential exhaust points (the outlet 110, the inlet 150 and the joint between the housing portions 102, 104), the skilled artisan will appreciate that, in accordance with some aspects of the invention, one exhaust point can suffice for achieving the function of the subsequent steps.

The initial liquid form of reagent is frozen 530 within the pack 100. For example, the partially assembled pack 100 can be dipped into a bath of acetone chilled with dry ice. This method was applied using an acetone bath temperature of about 78° C. The skilled artisan will readily appreciate a number of other suitable methods of freezing the initial liquid form of reagent. For example, the pack can be temporarily sealed for the freezing step, enabling a wider variety of freezing methods. The ratcheting plunger design of the embodiments above is particularly well adapted for such temporary sealing.

Following freezing 530, the frozen solution or suspension is subjected to vacuum 540 for sufficient time to vaporize the liquid component of the initial liquid reagent. Under laboratory conditions in a simple vacuum flask, this process consumed 12 hours. It will be understood that the process would ordinarily be conducted in batch under commercial conditions with high vacuum chambers. After the vacuum process, the dry reagent bed 106 is left within the pack 100, preferably sandwiched between frits and having the compression component already loaded adjacent thereto.

Thereafter, the assembly of drug delivery device can be completed 550. In the illustrated embodiment, this involves compacting the upper and lower housing portions 104, 102 and attaching port covers over the inlet port 150 and outlet port 110, as discussed with respect to FIG. 5B.

Advantageously, the in situ lyophilization process described with respect to FIG. 14 greatly simplifies mass production of delivery devices. Rather separately lyophilizing and then loading dry reagent into individual delivery devices, loading in liquid form facilitates batch loading of the reagent. Moreover, in situ lyophilization also reduces risk of contamination of both the device and the reagent itself, as time and transportation between forming a dry reagent and loading it within a delivery device are eliminated.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims.

We claim:

1. A method of forming a device for delivering a fluid form of a reagent from a dried form of the reagent, the method comprising lyophilizing an initial fluid form of the reagent within the device, wherein lyophilizing comprises:

loading the fluid form of the reagent in an open housing; and inserting a compression component within the housing, wherein the compression component is positioned to exert pressure on the reagent.

2. The method of claim 1, wherein lyophilizing further comprises:

enclosing the fluid form of the reagent within the housing without sealing the housing;

freezing the fluid form of the reagent within the housing; and subjecting the frozen fluid form to vacuum.

3. The method of claim 2, wherein subjecting the frozen fluid form to vacuum comprises allowing vapor to escape the housing through at least one of a fluid inlet and a fluid outlet of the housing.

4. The method of claim 2, wherein freezing comprises immersing the housing in a sub-0° C. fluid.

5. The method of claim 2, wherein enclosing comprises fitting an inner housing portion within an outer housing portion.

6. The method of claim 2, further comprising sealing the housing after subjecting the frozen fluid form to vacuum.

7. A method of forming a device for delivering a fluid form of a reagent from a dried form of the reagent, the method comprising lyophilizing an initial fluid form of the reagent within the device, wherein lyophilizing comprises:

loading a fluid form of the reagent in an open housing, wherein loading comprises sandwiching the fluid form between hydrophobic, porous fits;

enclosing the fluid form of the reagent within the housing without sealing the housing;

freezing the fluid form of the reagent within the housing; and subjecting the frozen fluid form to vacuum.

8. A method of forming a device for delivering a fluid form of a reagent from a dried form of the reagent, the method comprising lyophilizing an initial fluid form of the reagent within the device and inserting a compression component into the device to exert pressure on a dry reagent bed formed by the lyophilizing.

9. The method of claim 8, further comprising sealing the housing after inserting the compression component.

* * * * *

UNITED STATES PATENT AND TRADEMARK OFFICE
CERTIFICATE OF CORRECTION

PATENT NO. : 6,916,305 B2 Page 1 of 1
APPLICATION NO. : 10/339715
DATED : July 12, 2005
INVENTOR(S) : Eugene C. Jones and Michael A. Taylor It is certified that error appears in the above-identified patent and that said Letters Patent is hereby corrected as shown below:

In Col. 14, line 28, Claim 7, please delete "fits" and insert --frits--, therefor.

Signed and Sealed this

Twenty-seventh Day of November, 2007

JON W. DUDAS
*Director of the United States Patent and Trademark Office*